United States Patent
Skatter et al.

(10) Patent No.: US 9,405,990 B2
(45) Date of Patent: Aug. 2, 2016

(54) X-RAY DIFFRACTION IMAGING SYSTEM WITH SIGNAL AGGREGATION ACROSS VOXELS CONTAINING OBJECTS AND METHOD OF OPERATING THE SAME

(71) Applicant: MORPHO DETECTION, LLC, Newark, CA (US)

(72) Inventors: Sondre Skatter, Oakland, CA (US); Matthew Allen Merzbacher, Oakland, CA (US); Geoffrey Harding, Hamburg (DE); Samit Kumar Basu, Fremont, CA (US); Gabriel Zienert, Hamburg (DE)

(73) Assignee: MORPHO DETECTION, LLC, Newark, CA (US)

( * ) Notice: Subject to any disclaimer, the term of this patent is extended or adjusted under 35 U.S.C. 154(b) by 0 days.

(21) Appl. No.: 14/463,459

(22) Filed: Aug. 19, 2014

(65) Prior Publication Data

US 2016/0055390 A1  Feb. 25, 2016

(51) Int. Cl.
*A61B 6/00* (2006.01)
*G01N 23/00* (2006.01)
(Continued)

(52) U.S. Cl.
CPC ............ *G06K 9/46* (2013.01); *G01N 23/20083* (2013.01); *G01T 1/00* (2013.01);
(Continued)

(58) Field of Classification Search
USPC ................. 382/128–131, 154, 190, 195, 305; 378/4, 86, 169, E13.006
See application file for complete search history.

(56) References Cited

U.S. PATENT DOCUMENTS 5,007,072 A * 4/1991 Jenkins ................ G01V 5/0025
378/57
5,612,988 A * 3/1997 Martens ............... G01N 23/201
378/86
(Continued)

FOREIGN PATENT DOCUMENTS

EP  0556887 A1  8/1993
EP  2075570 A1  7/2009
(Continued)

OTHER PUBLICATIONS

Harding et al. "X-ray diffraction imaging with the Multiple Inverse Fan Beam topology: Principles, performance and potential for security screening" Applied Radiation and Isotopes 70 (2012) pp. 1228-1237 (pp. 1-10).*
(Continued)

*Primary Examiner* — Chan Park
*Assistant Examiner* — Mia M Thomas
(74) *Attorney, Agent, or Firm* — Armstrong Teasdale LLP

(57) ABSTRACT

A method of performing a security inspection of a container including a plurality of objects includes irradiating the container with polychromatic x-rays, reconstructing a 4-D voxelized representation defining a momentum transfer spectrum, and generating a 3-D image by determining a single value at each voxel as a function of the momentum transfer spectrum. The method further includes segmenting the voxels into segments of contiguous voxels that map onto at least one object. The method also includes computing an aggregated momentum transfer spectrum over at least a portion of the contiguous voxels through at least one of aggregating the spectra of the contiguous voxels for each segment and defining a supervoxel that includes voxels with the object exclusively and voxels in a neighborhood, regardless of association with the object. The method further includes classifying the object as one of a threat and a non-threat based on the aggregated momentum transfer spectrum.

22 Claims, 15 Drawing Sheets

(51) Int. Cl.
| | |
|---|---|
| G06K 9/46 | (2006.01) |
| G06T 7/00 | (2006.01) |
| G06T 15/08 | (2011.01) |
| G06T 5/00 | (2006.01) |
| G06K 9/62 | (2006.01) |
| G01N 23/20 | (2006.01) |
| G01T 1/00 | (2006.01) |
| G01V 5/00 | (2006.01) |

(52) U.S. Cl.
CPC .......... G01V 5/0025 (2013.01); G01V 5/0041 (2013.01); G06K 9/6267 (2013.01); G06T 5/001 (2013.01); G06T 7/0079 (2013.01); G06T 15/08 (2013.01); *G01N 2223/206* (2013.01); *G01N 2223/401* (2013.01); *G01N 2223/405* (2013.01); *G01N 2223/41* (2013.01); *G01N 2223/423* (2013.01); *G01N 2223/639* (2013.01); *G01N 2223/643* (2013.01); *G06T 2207/10116* (2013.01)

(56) References Cited

U.S. PATENT DOCUMENTS

| | | | | |
|---|---|---|---|---|
| 5,812,630 | A * | 9/1998 | Blaffert | G01N 23/201 378/57 |
| 6,018,562 | A * | 1/2000 | Willson | G01N 23/087 378/57 |
| 6,359,669 | B1 * | 3/2002 | Dehmlow | G02F 1/133512 349/110 |
| 6,470,067 | B1 * | 10/2002 | Harding | A61B 6/032 378/19 |
| 7,738,729 | B2 * | 6/2010 | Harding | G06T 11/008 378/51 |
| 7,756,249 | B1 | 7/2010 | Harding | |
| 7,787,591 | B2 | 8/2010 | Harding et al. | |
| 7,835,495 | B2 | 11/2010 | Harding | |
| 8,139,717 | B2 | 3/2012 | Harding et al. | |
| 2002/0150202 | A1 * | 10/2002 | Harding | A61B 6/032 378/16 |
| 2006/0104414 | A1 | 5/2006 | Mayo | |
| 2006/0140340 | A1 * | 6/2006 | Kravis | G01N 23/20 378/57 |
| 2006/0159227 | A1 * | 7/2006 | Harding | G01V 5/0025 378/86 |
| 2006/0239406 | A1 * | 10/2006 | Harding | G01V 5/0025 378/86 |
| 2007/0189444 | A1 * | 8/2007 | Van Steven-Daal | A61B 6/032 378/6 |
| 2008/0101681 | A1 * | 5/2008 | Schmiegel | G01V 5/0008 382/141 |
| 2008/0123895 | A1 * | 5/2008 | Gable | G06T 7/004 382/100 |
| 2008/0193002 | A1 * | 8/2008 | Ying | G01V 5/0008 382/131 |
| 2009/0034790 | A1 * | 2/2009 | Song | G06T 7/0002 382/103 |
| 2009/0168963 | A1 | 7/2009 | Harding | |
| 2009/0214857 | A1 * | 8/2009 | Itoh | C23C 16/403 428/336 |
| 2010/0220281 | A1 * | 9/2010 | Hones | G02C 7/021 351/44 |
| 2010/0226478 | A1 * | 9/2010 | Harding | G21K 1/025 378/70 |
| 2010/0329424 | A1 | 12/2010 | Harding et al. | |
| 2010/0329532 | A1 * | 12/2010 | Masuda | G01N 23/046 382/132 |
| 2011/0188632 | A1 * | 8/2011 | Harding | G01V 5/0016 378/86 |
| 2012/0263275 | A1 | 10/2012 | Harding et al. | |
| 2013/0182927 | A1 * | 7/2013 | Jang | G06T 11/006 382/131 |
| 2013/0259347 | A1 * | 10/2013 | Schmitt | A61B 6/032 382/131 |
| 2014/0247920 | A1 * | 9/2014 | Marks | G01N 23/201 378/87 |
| 2014/0307854 | A1 * | 10/2014 | Lauridsen | G01N 23/207 378/73 |
| 2014/0348298 | A1 * | 11/2014 | Ghammraoui | G01N 23/20091 378/73 |
| 2015/0025343 | A1 * | 1/2015 | Gareau | A61B 5/6898 600/328 |
| 2015/0160354 | A1 * | 6/2015 | Mertens | G01N 23/046 378/9 |

FOREIGN PATENT DOCUMENTS

| | | | | |
|---|---|---|---|---|
| GB | 2008/050358 | * | 5/2008 | ............ G01N 23/04 |
| WO | 2010051366 A2 | | 5/2010 | |
| WO | 2010051366 A3 | | 5/2010 | |

OTHER PUBLICATIONS

Erdogan, S.T. et al., "Determination of Aggregate Shape Properties Using X-ray Tomographic Methods and the Effect of Shape on Concrete Rheology," Research Report ICAR 106-1, International Center for Aggregates Research, The University of Texas at Austin, Austin, Texas, Aug. 2005—document split into two parts—Part 1 of 2 (160 pgs).

Tirodkar, A.A., "A Multi-Stage Algorithm for Enhanced X-Ray Image Segmentation," International Journal of Engineering Science and Technology (IJEST), vol. 3, No. 9, Sep. 2011, pp. 7056-7065.

Chen, F.F. et al., "Fast 3D Object Segmentation in X-ray Tomography," 18th World IMACS/MODSIM Congress, Cairns, Australia, Jul. 13-17, 2009 (http://www.mssanz.org.au/modsim09/C5/chen_ff.pdf), pp. 996-1002.

Erdogan, S.T. et al., "Determination of Aggregate Shape Properties Using X-ray Tomographic Methods and the Effect of Shape on Concrete Rheology," Research Report ICAR 106-1, International Center for Aggregates Research, The University of Texas at Austin, Austin, Texas, Aug. 2005—document split into two parts—Part 2 of 2 (159 pgs).

Harding, G. et al., "X-ray diffraction computer tomography," Medical Physics, vol. 14, No. 4, Jul./Aug. 1987, New York, NY, USA, pp. 515-525.

Harding, G. et al., "X-ray Diffraction Imaging for Explosives Detection," Chapter 8 in "Counterterrorist Detection Techniques of Explosives," 2007, Elsevier, pp. 199-235.

Cozzini, C. et al., "Modeling Scattering for Security Applications: a Multiple Beam X-Ray Diffraction Imaging System," 2012 IEEE Nuclear Science Symposium and Medical Imaging Conference Record (NSS/MIC), IEEE, 2012, pp. 74-77.

Extended European search report and opinion, dated Jan. 15, 2016, for copending EP patent application No. EP 15002417.2 (8 pgs.).

* cited by examiner

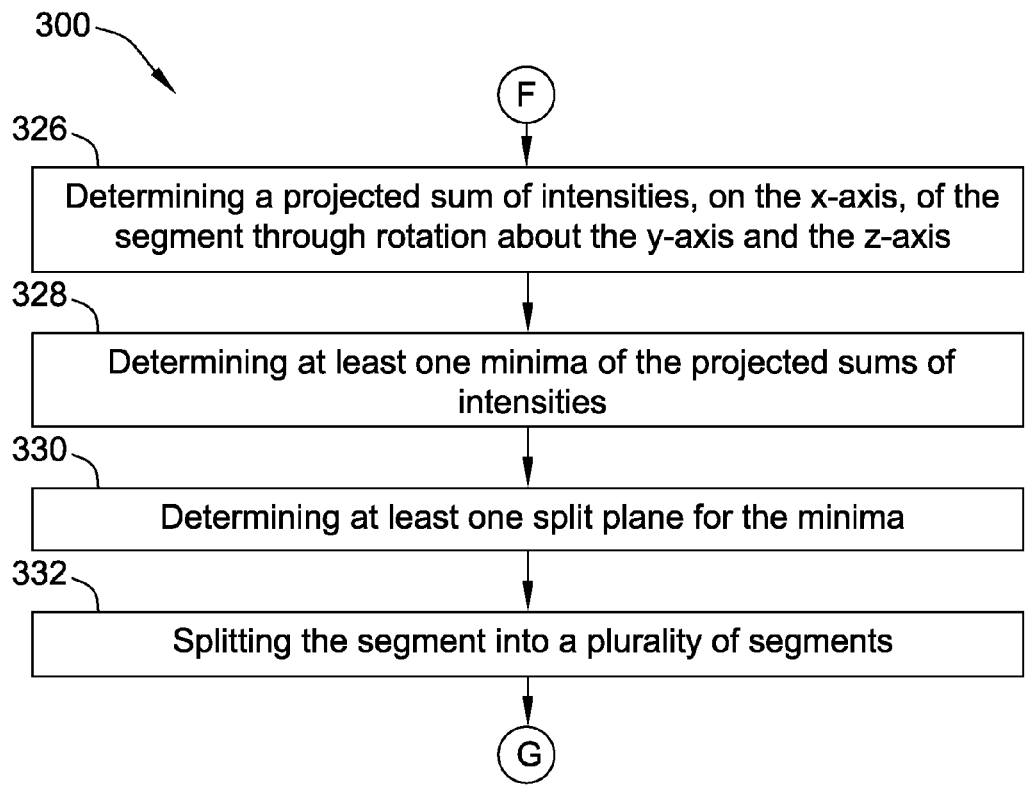
FIG. 15
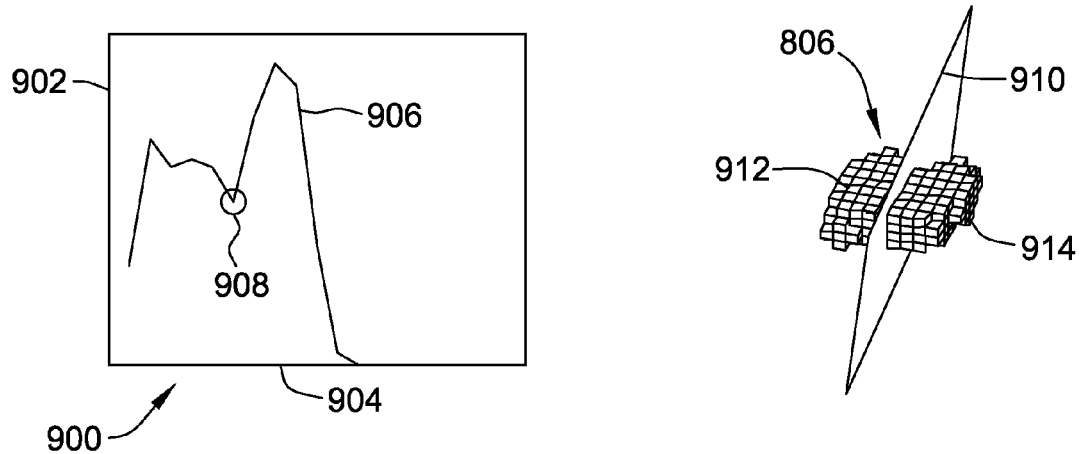
FIG. 16
FIG. 17

X-RAY DIFFRACTION IMAGING SYSTEM WITH SIGNAL AGGREGATION ACROSS VOXELS CONTAINING OBJECTS AND METHOD OF OPERATING THE SAME

STATEMENT REGARDING FEDERALLY SPONSORED RESEARCH & DEVELOPMENT

This invention was made with United States (U.S.) Government support under contract number HSHQDC-11-C-00014 awarded by the Department of Homeland Security (DHS). The U.S. Government may have certain rights in this invention.

BACKGROUND

The embodiments described herein relate generally to a system that employs x-ray diffraction imaging (XDI) and, more particularly, to an XDI system that identifies objects through aggregation of signals in multiple contiguous voxels.

Known security detection systems are used at travel checkpoints to inspect carry-on and/or checked bags for concealed weapons, narcotics, and/or explosives. At least some known security detection systems include x-ray imaging systems. In an x-ray imaging system, an x-ray source transmits x-rays through an object or a container, such as a suitcase, towards a detector, and the detector output is processed to identify one or more objects and/or one or more materials in the container.

At least some known XDI systems provide an improved discrimination of materials, as compared to that provided by other known x-ray imaging systems, by measuring d-spacings between lattice planes of micro-crystals in materials. Further, x-ray diffraction may yield data from a molecular interference function that may be used to identify other materials, such as liquids, in a container.

Known multi-detector inverse fan beam (MIFB) XDI systems feature an x-ray multisource emitting a multiplicity of polychromatic x-ray beams, such that each object voxel is irradiated from several different directions. These systems measure spatially-resolved x-ray diffraction profiles of the constituent voxels of inhomogeneous, extended objects. Such MIFB XDI systems generate a three-dimensional (3D) volumetric map, or image, where each voxel within the image includes the polychromatic energy spectrum, i.e., the momentum transfer profile for coherent scatter signals originating from each voxel. Some of these known MIFB XDI systems use relatively small voxels to improve visual resolution of smaller object features. However, as defined by the number of photons measured per voxel, the signal level from each voxel is very low. In general, performance of XDI systems decreases significantly when there are less than 100 photons per voxel. In some known XDI systems, the photon count is in the range between 0 and 25 photons per voxel.

Therefore, due to these low signal levels, it is difficult to establish reliable spectra for accurate material characterization in individual voxels. Objects of interest typically occupy multiple contiguous voxels and such objects of interest may be positioned proximate and/or adjacent to each other. A simple aggregation of signals from adjacent, or nearby voxels may provide sufficient material spectra to accurately identify a substance of interest. However, if the selection of combined voxels includes voxels with photons scattered from different materials, then the resulting spectrum will be a mixture and it may not be possible to identify the materials. In addition, visual discrimination of proximate and/or adjacent objects of interest may be difficult to generate.

BRIEF DESCRIPTION

In one aspect, a computer-implemented method of performing a security inspection of a container including a plurality of objects therein is provided. The method uses a computing device including at least one processor coupled to a memory device. The method includes irradiating the container with polychromatic x-rays and reconstructing, using the computing device, a four-dimensional (4-D) voxelized representation of a plurality of scatter cross-sections within the container. The 4-D voxelized representation includes a plurality of voxels. The first three dimensions represent a spatial location of each voxel of the plurality of voxels and the fourth dimension represents a plurality of momentum transfer values defining a momentum transfer spectrum of the container. The method also includes generating at least one three-dimensional (3-D) image by determining a single value at each voxel of the plurality of voxels as a function of the momentum transfer spectrum. The method further includes segmenting the plurality of voxels into a plurality of segments of contiguous voxels. Each segment of the plurality of segments includes a plurality of contiguous voxels. At least a portion of the plurality of segments at least partially maps onto at least one object of the plurality of objects. The method also includes computing an aggregated momentum transfer spectrum over the at least a portion of the plurality of contiguous voxels by using the at least a portion of the plurality of segments as guides for aggregation. The method further includes classifying the aggregated momentum transfer spectrum as one of threat and non-threat and distinguishing the at least one object as one of a threat segment and a non-threat segment based on the aggregated momentum transfer spectrum.

In another aspect, an x-ray diffraction imaging (XDI) system is provided. The XDI system includes at least one x-ray source configured to irradiate a container including a plurality of objects therein with polychromatic x-rays. The system also includes at least one detector configured to detect scattered x-rays after the polychromatic x-rays have passed through the container. The system further includes a computing device coupled to the at least one detector. The computing device includes at least one processor and a memory device coupled to the at least one processor. The at least one processor is configured to reconstruct a four-dimensional (4-D) voxelized representation of a plurality of scatter cross-sections within the container, wherein the 4-D voxelized representation includes a plurality of voxels. The first three dimensions represent a spatial location of each voxel of the plurality of voxels and the fourth dimension represents a plurality of momentum transfer values defining a momentum transfer spectrum of the container. The at least one processor is also configured to generate at least one three-dimensional (3-D) image by determining a single value at each voxel of the plurality of voxels as a function of the momentum transfer spectrum. The at least one processor is further configured to segment the plurality of voxels into a plurality of segments of contiguous voxels. Each segment of the plurality of segments includes a plurality of contiguous voxels. At least a portion of the plurality of segments at least partially maps onto at least one object of the plurality of objects. The at least one processor is also configured to compute an aggregated momentum transfer spectrum over the at least a portion of the plurality of contiguous voxels by using the at least a portion of the plurality of segments as guides for aggregation. The at least one processor is further configured to classify the aggregated momentum transfer spectrum as one of threat and non-threat and distinguish the at least one object as one of a threat segment and a non-threat segment based on the aggregated momentum transfer spectrum.

In a further aspect, one or more computer-readable storage media having computer-executable instructions embodied thereon is provided. When executed by at least one processor, the computer-executable instructions cause the at least one processor to reconstruct a four-dimensional (4-D) voxelized representation of a plurality of scatter cross-sections within the container. The 4-D voxelized representation includes a plurality of voxels. The first three dimensions represent a spatial location of each voxel of the plurality of voxels and the fourth dimension represents a plurality of momentum transfer values defining a momentum transfer spectrum of the container. The computer-executable instructions also cause the at least one processor to generate at least one three-dimensional (3-D) image by determining a single value at each voxel of the plurality of voxels as a function of the momentum transfer spectrum. The computer-executable instructions further cause the at least one processor to segment the plurality of voxels into a plurality of segments of contiguous voxels. Each segment of the plurality of segments includes a plurality of contiguous voxels. At least a portion of the plurality of segments at least partially maps onto at least one object of the plurality of objects. The computer-executable instructions also cause the at least one processor to compute an aggregated momentum transfer spectrum over the at least a portion of the plurality of contiguous voxels by using the at least a portion of the plurality of segments as guides for aggregation. The computer-executable instructions further cause the at least one processor to classify the aggregated momentum transfer spectrum as one of threat and non-threat and distinguish the at least one object as one of a threat segment and a non-threat segment based on the aggregated momentum transfer spectrum.

DRAWINGS

FIGS. 1-24 show exemplary embodiments of the systems and methods described herein.

FIG. 1 is a schematic view of an exemplary x-ray diffraction imaging (XDI) system in an X-Y plane;

FIG. 2 is a schematic view of an exemplary container including a plurality of objects;

FIG. 3 is a flow chart of an exemplary method of performing a security inspection of a container including a plurality of objects using the XDI system shown in FIG. 1;

FIG. 4 is a schematic view of an exemplary image, i.e., a four-dimensional (4-D) voxelized representation of the container shown in FIG. 2;

FIG. 5 is a continuation of the method from FIG. 3;

FIG. 6 is a schematic view of an exemplary three-dimensional (3-D) image of the container shown in FIG. 2 generated by determining a single value of scatter strength at each voxel shown in the 4-D voxelized representation shown in FIG. 4;

FIG. 7 is a continuation of the method from FIG. 5;

FIG. 8 is a schematic view of an exemplary image of the container shown in FIG. 2 generated by filtering the image shown in FIG. 6;

FIG. 9 is a continuation of the method from FIG. 7;

FIG. 10 is a schematic view of an exemplary image of the container shown in FIG. 2 generated by thresholding the image shown in FIG. 8;

FIG. 11 is a continuation of the method from FIG. 9;

FIG. 12 is a schematic view of an exemplary image of the container shown in FIG. 2 generated by labeling the image shown in FIG. 10;

FIG. 13 is a continuation of the method from FIG. 11;

FIG. 14 is a schematic view of the image shown in FIG. 12 with orthogonal x-, y-, and z-axes;

FIG. 15 is a continuation of the method from FIG. 13;

FIG. 16 is a graphical representation of sums of intensities of a segment of contiguous voxels projected on an x-axis through rotation of the segment about an orthogonal y-axis and z-axis;

FIG. 17 is a schematic view of a segment of contiguous voxels with a split plane extending therethrough;

FIG. 18 is a continuation of the method from FIG. 15;

FIG. 19 is a schematic representation of an exemplary image of the container shown in FIG. 2 with separated segments of contiguous voxels;

FIG. 20 is a continuation of the method from FIG. 18 for some embodiments;

FIG. 21 is a continuation of the method from FIG. 18 for yet some further embodiments;

FIG. 22 is a continuation of the method from FIGS. 20 and 21;

FIG. 23 is a schematic and graphical view of an exemplary image using the XDI system shown in FIG. 1; and FIG. 24 is an exemplary configuration of a database within the computing device shown in FIG. 1, along with other related computing components, which may be used to perform a security inspection of a container with the XDI system as described herein.

DETAILED DESCRIPTION

The x-ray diffraction imaging (XDI) systems described herein facilitate cost-effective enhanced identification of materials of interest with a suitably high probability of detection ($P_D$) and low probability of false alarm, i.e., false positive ($P_{FA}$). Specifically, in contrast to many known security scanning systems, the XDI security screening systems as described herein facilitate segmentation of multiple contiguous voxels into segments that may include materials of interest. The initial steps prior to segmentation include generating a scatter strength value for each voxel and filtering the signals for each voxel, thereby decreasing the noise level and improving the homogeneity of those voxels including a single material. The segmentation process includes filtering out voxels with scatter strengths less than a predetermined threshold value that is based on the materials of interest, thereby leaving contiguous voxels with missing voxels in between. The segmentation process also includes a labeling step, where some voxels are retained and some voxels are disregarded, i.e., excluded. The retained voxels are connected and the connected voxels form "islands", i.e., segments of contiguous voxels between the excluded voxels. The segmentation process further includes splitting the segmented segments of contiguous voxels into smaller, individual objects. Moreover, the segmentation process includes computing the spectra for each object through aggregating the spectra of the voxels therein.

As such, the XDI security screening systems as described herein facilitate resolution of individual objects and classification into threat/no threat substances through advanced image segmentation as a function of aggregating the spectra of contiguous voxels. Specifically, the XDI security screening systems described herein facilitate improved resolution of objects/substances of interest positioned proximate and/or adjacent to each other through joining voxels with predetermined associating characteristics, disregarding voxels without such characteristics, and separating the joined voxels. More specifically, the systems described herein facilitate improved determinations of which voxels to join. Therefore, efficient and effective detection of substances, such as the classes of liquid substances of interest, in cabin baggage screening (CBS) and hold baggage screening (HBS) systems is enhanced.

Figure 1:
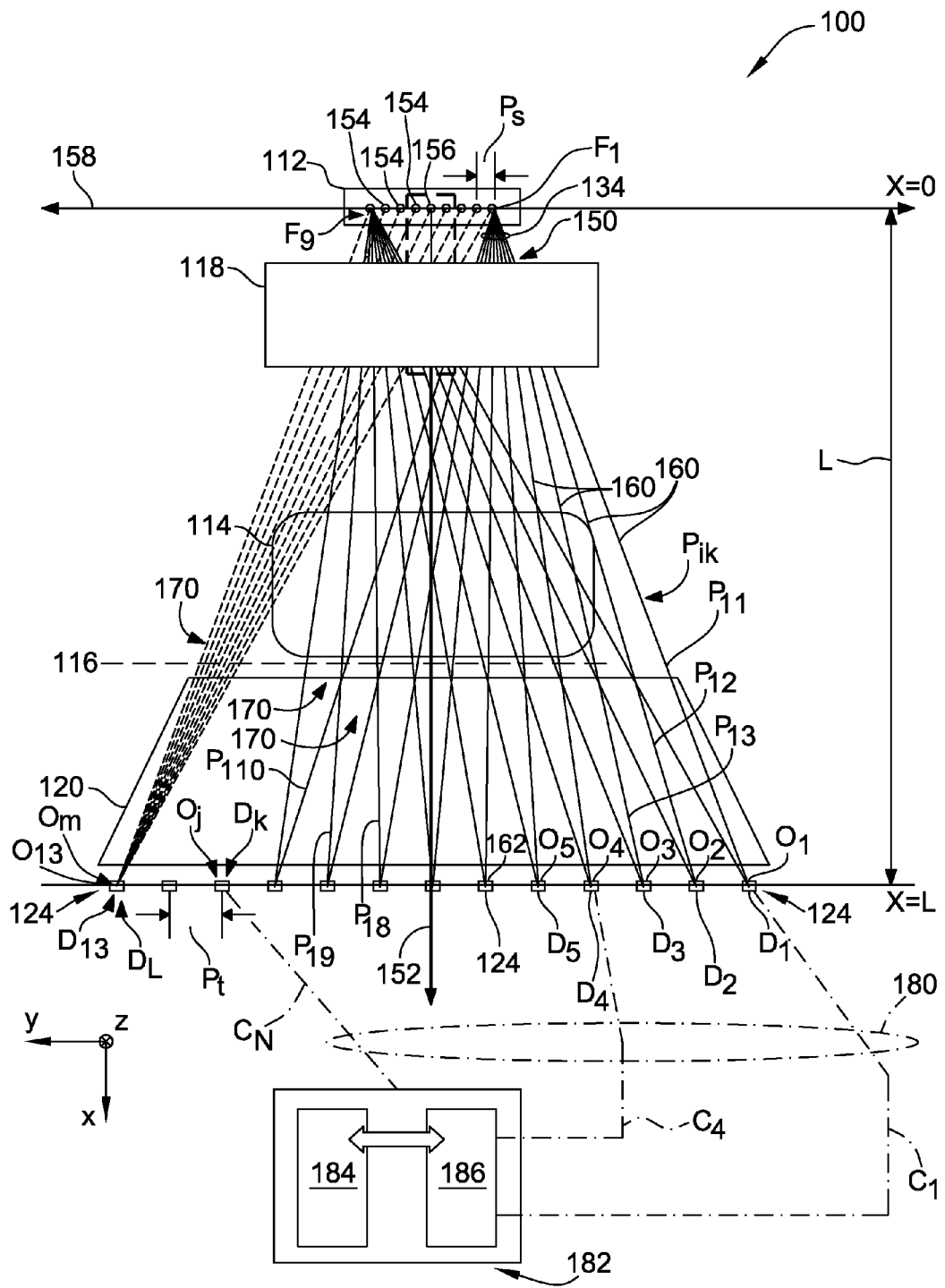

FIG. 1 is a schematic view of an exemplary x-ray diffraction imaging (XDI) system 100 in an X-Y plane. In the exemplary embodiment, XDI system 100 is a multi-detector inverse fan beam x-ray diffraction imaging (MIFB XDI) system. Alternatively, system 100 is any XDI system that enables operation of system 100 as described herein. XDI system 100 includes a multi-focus x-ray source (MFXS) 112, an examination area 114, a support 116 configured to support an object, a primary collimator 118, and a secondary collimator 120. XDI system 100 also includes two types of detectors, an array of transmission detectors (not shown) and a plurality of discrete coherent x-ray scatter detectors 124, which are energy-resolving photon counting detectors. The transmission detectors are offset in a z-axis direction from coherent x-ray scatter detectors 124.

In the exemplary embodiment, MFXS 112 is configured to emit polychromatic x-ray radiation sequentially from a plurality of focus points, as described below, distributed along MFXS 112 in a direction substantially parallel to a y-axis perpendicular to the z-axis. In the exemplary embodiment, MFXS 112 has nine (9) focus points. In alternative embodiments, MFXS 112 has approximately 40 to 100 focus points. Also alternatively, MFXS 112 may include any suitable number of focus points that enables operation of XDI system 100 as described herein.

Further, in the exemplary embodiment, MFXS 112 is located on or coupled to an upper support surface, such as at or near a ceiling, while the transmission detectors and coherent x-ray scatter detectors 124 are located on, or coupled to, a lower support structure, such as at or near a floor. In an alternative embodiment, MFXS 112 is located on or coupled to a lower support structure, such as at or near a floor, while the transmission detectors and coherent x-ray scatter detectors 124 are located on or coupled to an upper support surface, such as at or near a ceiling. Further, in the exemplary embodiment, MFXS 112, the transmission detectors and coherent x-ray scatter detectors 124 are stationary, support 116 is a conveyor belt capable of movement backward and forward in a direction substantially parallel to the z-axis, and examination area 114 is a baggage tunnel through which the conveyor belt moves. In an alternative embodiment, MFXS 112, the transmission detectors and coherent x-ray scatter detectors 124 are capable of coordinated movement at least in a direction substantially parallel to the z-axis, and support 116 is stationary. In certain alternative embodiments, MFXS 112, the transmission detectors, coherent x-ray scatter detectors 124, and support 116 are all capable of movement.

In the exemplary embodiment, MFXS 112 is configured to emit, through primary collimator 118, a set of polychromatic x-ray pencil beams 134, from each focus point of MFXS 112. A portion of the polychromatic x-ray radiation from each pencil beam 134 typically is scattered in various directions upon contact with a container (not shown) in examination area 114. Secondary collimator 120 is configured to facilitate ensuring that a portion of scattered radiation (not shown) arriving at each coherent x-ray scatter detector 124 has a constant scatter angle with respect to the corresponding pencil beam 134 from which the scattered radiation originated.

In the exemplary embodiment, a multi-detector inverse fan beam 150 formed from a set of polychromatic x-ray pencil beams 134 is projected along x-axis 152 onto the X-Y plane. More specifically, pencil beams 134 of fan beam 150 fan out in the X-Y plane. Pencil beams 134 of fan beam 150 also fan out in the X-Z plane. In one embodiment, MFXS 112 emits radiation sequentially from a plurality of focus points 154. More specifically, MFXS 112 includes an anode 156 and a plurality of focus points 154 arranged along a length of anode 156 collinear with a y-axis 158 of MFXS 112. Each focus point 154 is sequentially activated to emit an x-ray fan beam. For example, a focus point $F_1$ emits fan beam MIFB 150 that extends between and is detected by coherent x-ray scatter detector $D_1$ through and including coherent x-ray scatter detector $D_{13}$ and includes a plurality of pencil primary beams 160. Focus points 154 are denoted $F_1, F_2, \ldots F_i, \ldots F_n$ with a running index i. Primary collimator 118 is configured to select from the radiation emitted at each focus point 154, primary beams that are directed to a series of convergence points 162 labeled $O_1, O_2, \ldots, O_j, \ldots O_m$ with a running index j regardless of which focus point 154 is activated. Ten primary beams 160 are shown in FIG. 1 with each primary beam 160 emitted from focus point $F_1$ directed to a corresponding convergence point $O_1, O_2, \ldots, O_j, \ldots O_{13}$ positioned along a line parallel to y-axis 158 at a coordinate X=L with focus point $F_1$ activated.

A plurality of discrete coherent x-ray scatter detectors 124 labeled discrete coherent x-ray scatter detectors $D_1, D_2, \ldots D_k, \ldots D_L$ with a running index k are positioned at a suitable or desirable distance in a direction along the Z-axis from a corresponding convergence point 162 to record coherent scatter from primary beam $P_{ij}$ in discrete coherent x-ray scatter detector $D_k$. A combination of MFXS 112 and discrete coherent x-ray scatter detectors 124 facilitates examining a volume of an object positioned within examination area 114 without any dead area from which no XDI signal is detected or measured.

As primary beams 160 labeled $P_{ij}$ propagate through an object (not shown) positioned within examination area 114, primary beam $P_{ij}$ interacts with the object to produce coherent scatter that may be detected in coherent x-ray scatter detectors $D_{j+1}, D_{j+2}, D_{j-1}$, and/or $D_{j-2}$, for example. Primary beams $P_{11}, P_{12}, P_{13}, P_{14}, P_{15}, \ldots P_{1k}, \ldots P_{1L}$, are emitted from focus point $F_1$ and directed to corresponding convergence points $O_1, O_2, O_3, O_4, O_5, \ldots, O_j, \ldots O_m$, respectively. As each primary beam $P_{11}, P_{12}, P_{13}, P_{14}, P_{15}, \ldots P_{1k}, \ldots P_{1L}$ moves through examination area 114, each primary beam $P_{11}, P_{12}, P_{13}, P_{14}, P_{15}, \ldots P_{1k}, \ldots P_{1L}$ collides with and/or interacts with an object (not shown) positioned within examination area 114 to produce coherent scatter (not shown) that is detectable at one or more coherent x-ray scatter detectors $D_1, D_2, D_3, D_4, D_5, \ldots D_k, \ldots D_L$ for example.

In the exemplary embodiment, MFXS 112 is positioned on the y-axis (x=0) of a Cartesian coordinate system. Each focus point 154 has a position on a grid having a pitch, $P_s$. Further, convergence points 162 lie parallel to the y-axis at coordinate X=L, and each convergence point 162 has a position on a grid having a pitch, $P_t$. In a particular embodiment, for an XDI checked baggage screening system, L has a value of about 2000 millimeters (mm), $P_s$ has a value of about 20 mm, and $P_t$ has a value of about 200 mm. Alternatively, L, $P_s$, and $P_t$ have any values that enable operation of XDI system 100 as described herein.

A plurality of coherent x-ray scatter detectors 124 are positioned at the same y-coordinate as convergence points 162. One pair of coherent x-ray scatter detectors 124 may be associated with a corresponding convergence point 162 with the pair of coherent x-ray scatter detectors 124 positioned on both sides of the X-Y plane. In a further embodiment, thirteen (13) convergence points are used to allow for several convergence point position arrangements to incorporate a different number of coherent x-ray scatter detectors 124. If all convergence points 162 have detector pairs then XDI system 100 may include twenty-six (26) coherent x-ray scatter detectors 124. In alternative embodiments, fewer coherent x-ray scatter detectors 124 may be positioned at convergence point positions 1, 3, 5, 7, 9, 11, and 13, at convergence point positions 1, 4, 7, 10, and 13, or at convergence point positions 1, 5, 9, and 13 to account for manufacturing and/or cost constraints.

A left-most detector D13 detects a plurality of primary beams 160 labeled $P_{113}$, $P_{213}$, ... $P_{ik}$, ... $P_{913}$, alternatively referred to herein as an inverse fan beam bundle 170 of primary beams, from each focus point 154 denoted $F_1$, $F_2$, ... $F_i$, ... $F_9$ of MFXS 112 that are transmitted by primary collimator 118. Inverse fan beam bundle 170 is significantly narrower than a width of examination area 114. MFXS 112, as depicted in FIG. 1 is not shown to scale for clarity's sake, and may be smaller than shown. Moreover, only 13 convergence points 162 are shown although, as described above, in practice the number of convergence points 162 can be much greater. Further, the scatter signal is proportional to a number of coherent x-ray scatter detectors 124 incorporated into XDI system 100.

Several inverse fan beam bundles 170 of primary beams directed towards a corresponding convergence point $O_j$ are detected by a corresponding coherent x-ray scatter detector $D_k$. During a scan of the object positioned within examination area 114, during which each focus point 154 of MFXS 112 is sequentially activated, the object section is completely irradiated and scatter signals are measured from an entire width of the object. In this embodiment, no mechanical movements are required to achieve a complete 2-D and/or 3-D scan of the object. MFXS 112 achieves this with only a small x-ray source dimension along the y-axis. In the exemplary embodiment, MFXS 112 has a length along the y-axis of less than about 500 mm. A small x-ray source dimension is advantageous from the viewpoints of cost and reliability.

As described above, XDI system 100 includes two types of detectors, i.e., an array of transmission detectors (not shown) and a plurality of discrete coherent x-ray scatter detectors 124, each individually labeled as $D_1$, $D_2$, $D_3$, $D_4$, $D_5$, ... $D_k$, ... $D_L$. The transmission detectors are offset in the z-axis direction from coherent x-ray scatter detectors 124. In the exemplary embodiment, the transmission detectors are charge integration detectors, while coherent x-ray scatter detectors 124 are pulse-counting energy-resolving detectors. The transmission detectors and each coherent x-ray scatter detector 124 are in electronic communication with a number of channels 180, for example, N number of channels $C_1$, ... $C_p$, ... $C_N$, with a running index p where N is selected based on the configuration of XDI system 100, and where only those channels C associated with coherent x-ray scatter detectors 124 are shown. Channels 180 electronically communicate data collected by the transmission detectors and each coherent x-ray scatter detector 124 to a computing device 182. In the exemplary embodiment, computing device 182 combines an output from the transmission detectors and an output from coherent x-ray scatter detectors 124 to generate information about the contents of an object positioned within examination area 114. For example, but not by way of limitation, computing device 182 may generate multiview projections and/or section images of a container (not shown) in examination area 114 that identify a location in the container of specific materials detected by XDI analysis.

In the exemplary embodiment, computing device 182 includes a processor 184 in communication with the transmission detectors and coherent x-ray scatter detectors 124 through a memory device 186. Processor 184 is programmed, i.e., configured to receive from coherent x-ray scatter detectors 124 output signals representative of the detected x-ray quanta and generate a distribution of momentum transfer values, x, from a spectrum of energy, E, of x-ray quanta within scattered radiation detected by coherent x-ray scatter detectors 124.

As used herein, the terms "processor" and "processing device" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, e.g., firmware, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Also, as used herein, the terms "software" and "firmware" are interchangeable, and include any computer program stored in memory for execution by personal computers, workstations, clients and servers.

Further, as used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Processor 184 and other processors (not shown) as described herein process information transmitted from a plurality of electrical and electronic devices that include, without limitation, coherent x-ray scatter detectors 124. Memory devices 186 and storage devices (not shown) store and transfer information and instructions to be executed by processor 184. Such memory devices 186 and storage devices can also be used to store and provide temporary variables, static (i.e., non-volatile and non-changing) information and instructions, or other intermediate information to processor 184 during execution of instructions by processor 184. Instructions that are executed include, but are not limited to, analysis of signals transmitted from coherent x-ray scatter detectors 124. The execution of sequences of instructions is not limited to any specific combination of hardware circuitry and software instructions.

Figure 2:
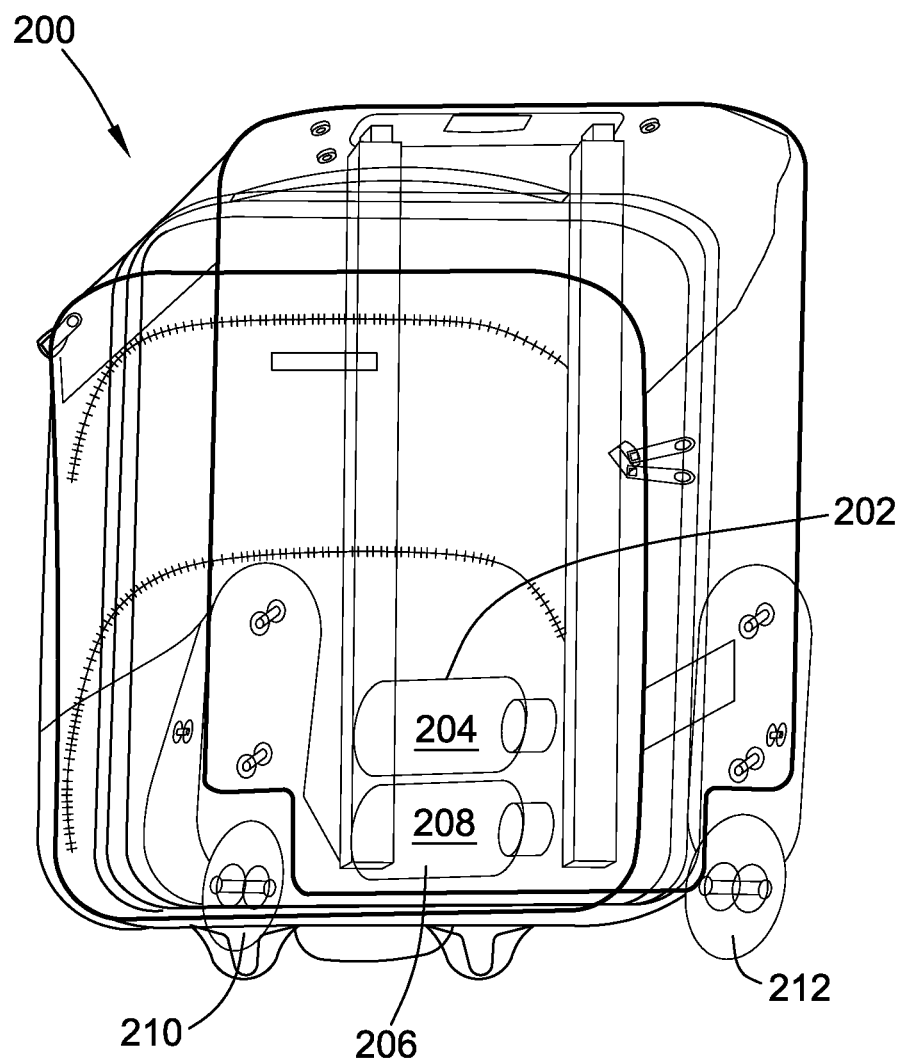

FIG. 2 is a schematic view of an exemplary container 200 including a plurality of objects. Specifically, the plurality of objects includes a first object 202 including a first substance 204 and a second object 206 including a second substance 208. In the exemplary embodiment, first object 202 and second object 206 are bottles. One of substances 204 and 208 is a non-threat substance and the other is a threat substance. Container 200 also includes a left wheel 210 and a right wheel 212. In the exemplary embodiment, container 200 is a piece of carry-on luggage that will be examined with an XDI-based cabin baggage screening (CBS) system or an XDI-based hold baggage screening (HBS) system. Alternatively, container 200 is any type container that is configured to include one or more objects therein, including, without limitation, shipping containers (e.g., cardboard boxes, plastic storage units, and wooden crates), large suitcases, and travel bags. The image of container 200 and objects 202 and 206 was at least partially generated through a high-resolution projection-type x-ray scanning device and is presented for illustrative and comparison purposes.

Figure 3:
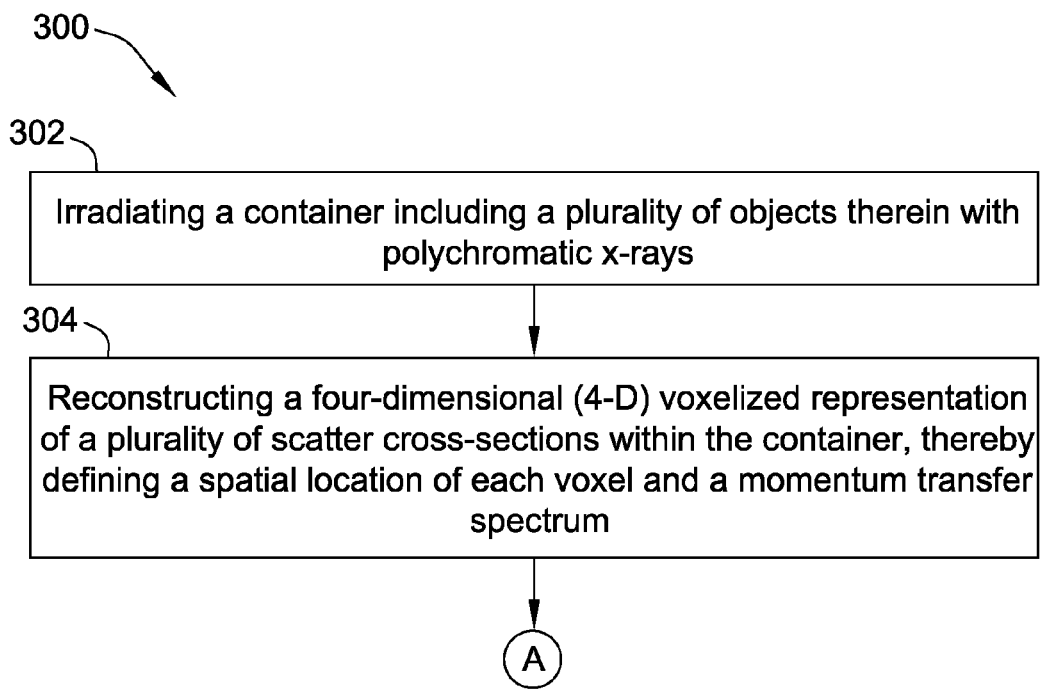

FIG. 3 is a flow chart of an exemplary method 300 of performing a security inspection of container 200 including plurality of objects 202 and 206 (all shown in FIG. 2) using XDI system 100 (shown in FIG. 1). Method 300 includes irradiating 302 container 200 with objects 202 and 206 and substances 204 and 208, respectively (shown in FIG. 2). Such irradiating 302 is performed with multi-detector inverse fan beam 150 formed from polychromatic x-ray pencil beams 134 generated by multi-focus x-ray source 112 (all shown in FIG. 1) with container 200 positioned on support 116 within examination area 114 (both shown in FIG. 1). Method 300 also includes reconstructing 304, using computing device 182 (shown in FIG. 1), a four-dimensional (4-D) voxelized representation of a plurality of scatter cross-sections within container 200, i.e., all spatial locations within container 200.

Figure 4:
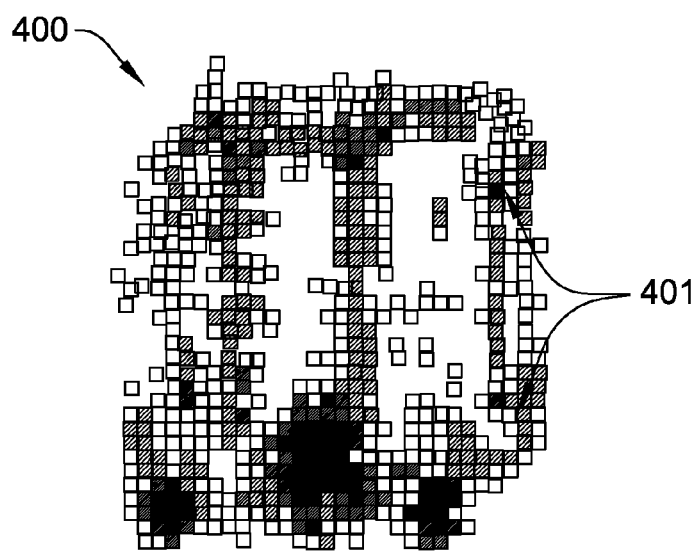

FIG. 4 is a schematic view of an exemplary image, i.e., a 4-D voxelized representation 400 of container 200 (shown in FIG. 2) that includes a plurality of voxels 401. The first three dimensions of 4-D voxelized representation 400 represent a spatial location of each of voxels 401. The fourth dimension represents a plurality of momentum transfer values defining a momentum transfer profile that further defines a momentum transfer spectrum as indicated through the shading of voxels 401. The apparent opaqueness of each of voxels 401 is proportional to the associated momentum transfer value. The terms momentum and, in plural, momenta, are typically used to indicate a momentum transfer value, that is, the amount of momentum transferred from a first particle to a second particle and/or the amount of momentum transferred from a first wave to a second wave, or, as used herein, an increase in a photonic momentum as a result of an interaction of a portion of objects 202 and 206 and substances 204 and 208, respectively, (shown in FIG. 1) with a scattered x-ray (not shown).

Figure 5:
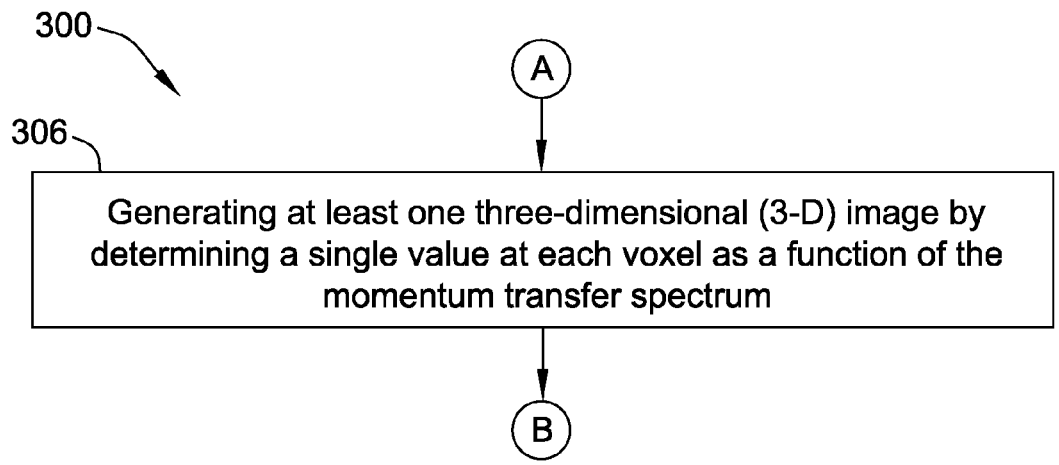

FIG. 5 is a continuation of method 300 from FIG. 3. Method 300 further includes generating 306 at least one three-dimensional (3-D) image by determining a single value at each voxel 401 as a function of the momentum transfer spectrum. To facilitate such 3-D image generation, the plurality of scatter cross-sections are summed over substantially all of the momentum transfer values within the momentum transfer spectrum for each individual voxel 401. Alternatively, other methods of computing a scalar value from a spectrum includes, without limitation, linear combination of the spectrum values, and any non-linear function that reduces the spectrum to a single value.

Figure 6:
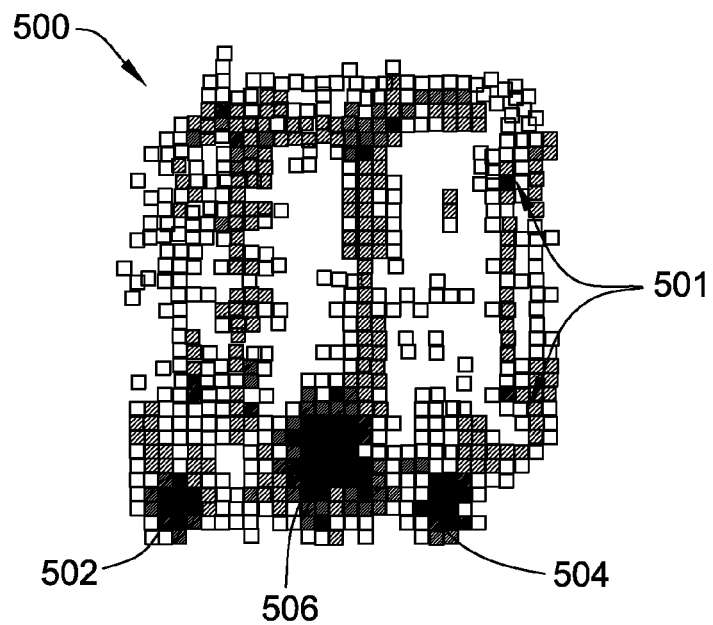

FIG. 6 is a schematic view of an exemplary 3-D image 500 of container 200 (shown in FIG. 2) generated by determining a single value of scatter strength at each voxel 401 shown in 4-D voxelized representation 400 (shown in FIG. 4). As such, 3-D image 500 includes a plurality of voxels 501 generated by determining the single value of scatter strength at each voxel 401 by summing, or integrating over substantially all of the momentum transfer values within the momentum transfer profile. Image 500 includes three dark spots 502, 504, and 506 that correspond to left wheel 210, right wheel 212, and objects 202 and 206, respectively (all shown in FIG. 2). As shown in FIG. 6, it is difficult to determine the actual identities of wheels 210 and 212 and objects 202 and 206.

Figure 7:
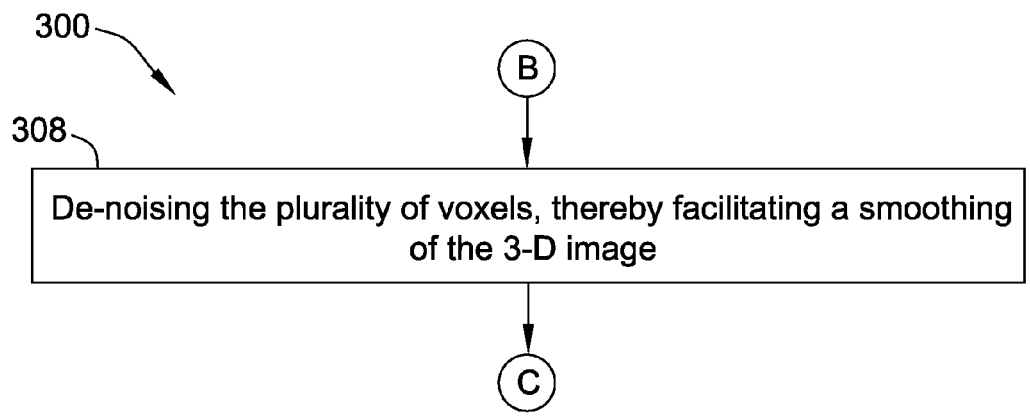

FIG. 7 is a continuation of method 300 from FIG. 5. Method 300 also includes de-noising 308 plurality of voxels 501 (shown in FIG. 6), thereby facilitating a smoothing of 3-D image 500 (shown in FIG. 5). Specifically, image 500 is subjected to predetermined filtering that facilitates smoothing image 500 such that it is less noisy.

Figure 8:
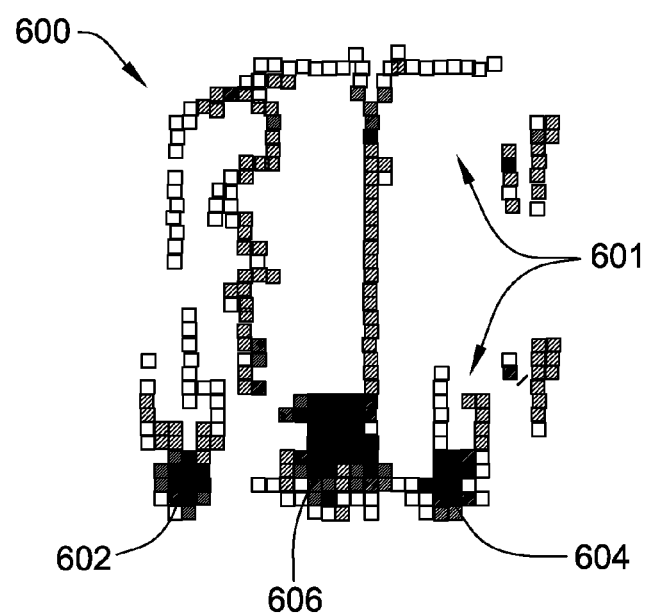

FIG. 8 is a schematic view of an exemplary image 600 of container 200 (shown in FIG. 2) generated by filtering image 500 (shown in FIG. 6). Image 600 includes a plurality of filtered voxels 601 and three dark spots 602, 604, and 606 that correspond to dark spots 502, 504, and 506, respectively (all shown in FIG. 6), that in turn, correspond to left wheel 210, right wheel 212, and objects 202 and 206, respectively (all shown in FIG. 2). It is still difficult to determine the actual identities of wheels 210 and 212 and objects 202 and 206. However, the filtering mechanism removes a large number of dark voxels 501 (shown in FIG. 6) not necessarily associated with wheels 210 and 212 and objects 202 and 206 such that dark spots 602, 604, and 606 are more contrasted with the remainder of voxels 601 as compared to dark spots 502, 504, and 506 and their contrast to the remainder of voxels 501.

Figure 9:
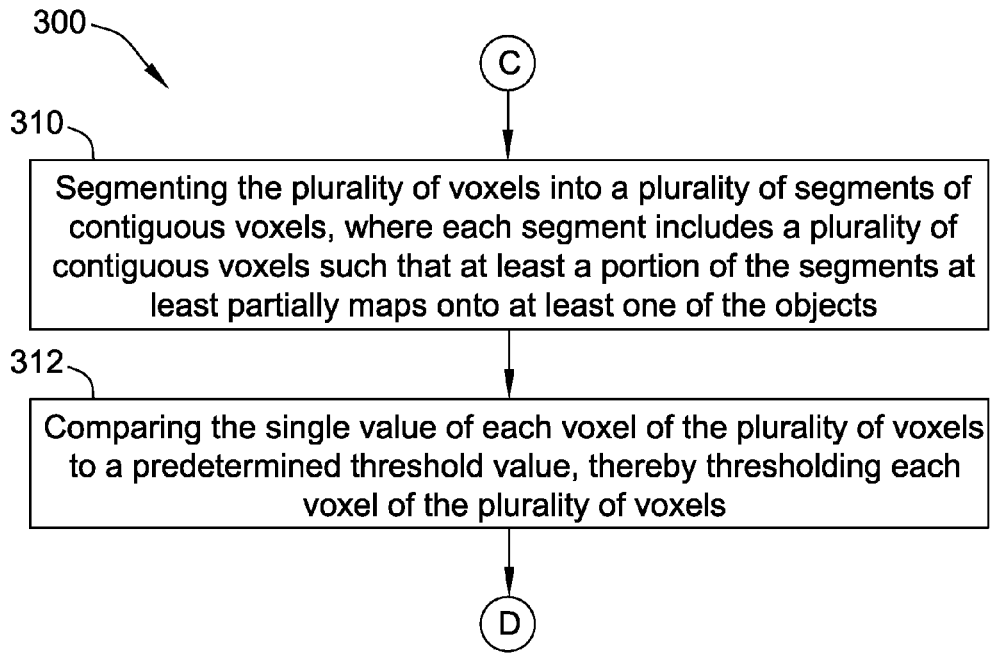

FIG. 9 is a continuation of method 300 from FIG. 7. Method 300 further includes segmenting 310 the plurality of voxels into a plurality of segments of contiguous voxels, where each segment of the plurality of segments includes a plurality of segments of contiguous voxels such that at least a portion of the plurality of segments at least partially maps onto at least one of objects 202 and 206 (shown in FIG. 2). As such, method 300 includes comparing 312 the single value of scatter strength of each voxel 601 (shown in FIG. 8) of plurality of voxels 601 to a predetermined threshold value, thereby thresholding each voxel 601 as a portion of segmenting 310.

Figure 10:
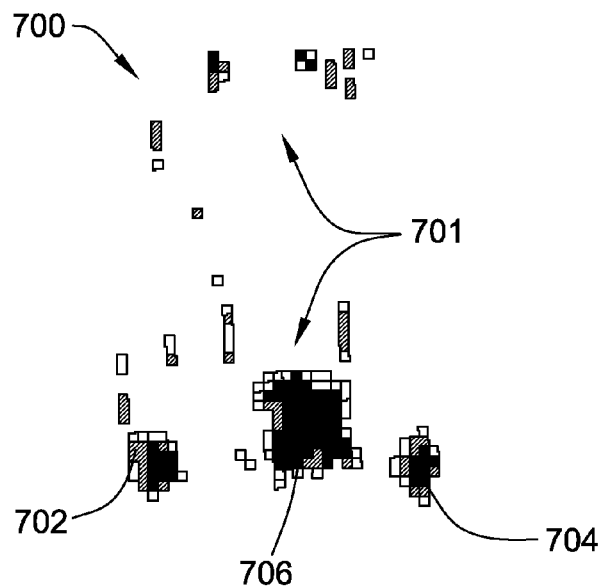

FIG. 10 is a schematic view of an exemplary image 700 of container 200 (shown in FIG. 2) generated by thresholding image 600 (shown in FIG. 8). Most of voxels 601 having relatively low values for scatter strength are removed from image 700 and only those voxels 601 with a scatter strength value above the threshold remain, i.e., are retained as voxels 701. As such, a plurality of segments of contiguous voxels 702, 704, and 706 are formed and are isolated from and contrasted with the remainder of voxels 701 as compared to dark spots 602, 604, and 606 and their contrast with the remainder of voxels 601.

Figure 11:
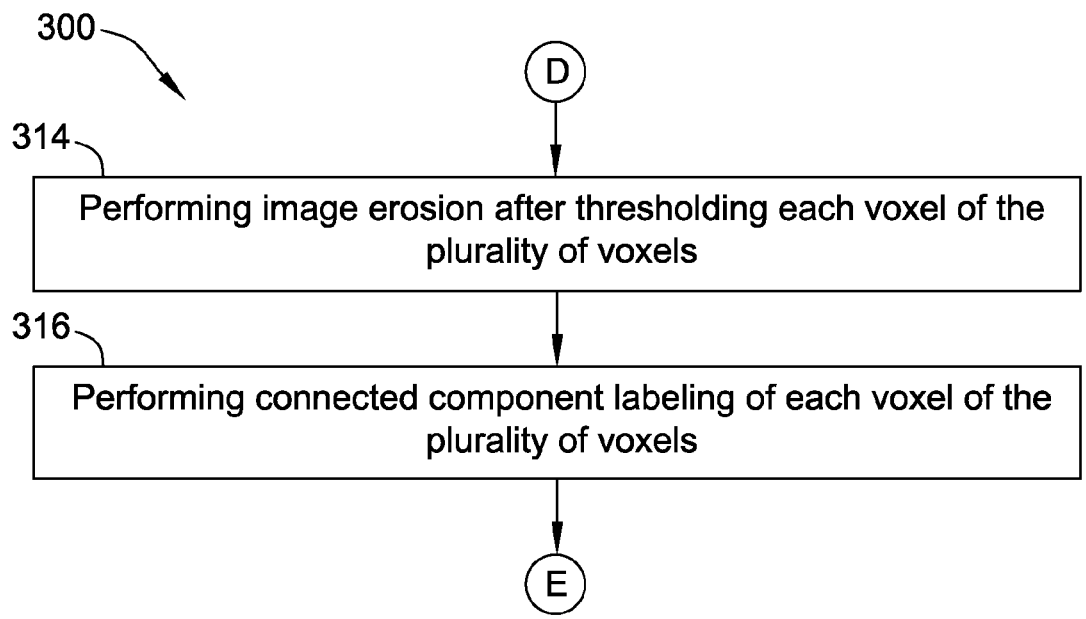

FIG. 11 is a continuation of method 300 from FIG. 9. Method 300 also includes performing an optional image erosion, i.e., eroding 314 image 700 after thresholding each voxel 701 as a portion of segmenting 310. Method 300 further includes performing connected component labeling 316 of each voxel 701 as a portion of segmenting 310. In alternative embodiments, method step 316 is performed before method step 314 and method step 316 is reperformed.

Figure 12:
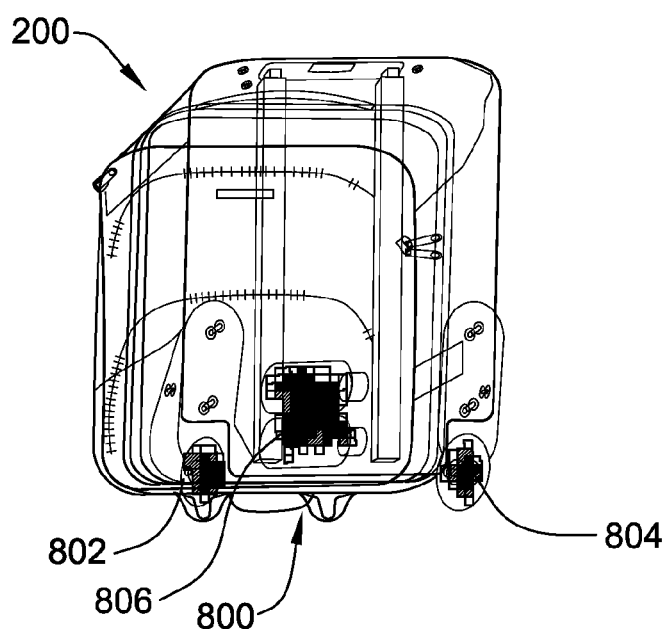

FIG. 12 is a schematic view of an exemplary image 800 of container 200 generated by labeling image 700 (shown in FIG. 10). More specifically, image 200 is superimposed over image 800 to better illustrate the remainder of method 300, including FIGS. 14, 19, and 23. As such, a plurality of segments of eroded and labeled contiguous voxels 802, 804, and 806 are formed from plurality of segments of contiguous voxels 702, 704, and 706 (shown in FIG. 1). Segment 806 represents objects 202 and 206, i.e., a pair of adjacent bottles. Since one of objects 202 and 206 includes a threat substance and the other includes a non-threat substance, segment 806 may provide an ambiguous detection or a non-detection during x-ray screening of container 200.

Figure 13:
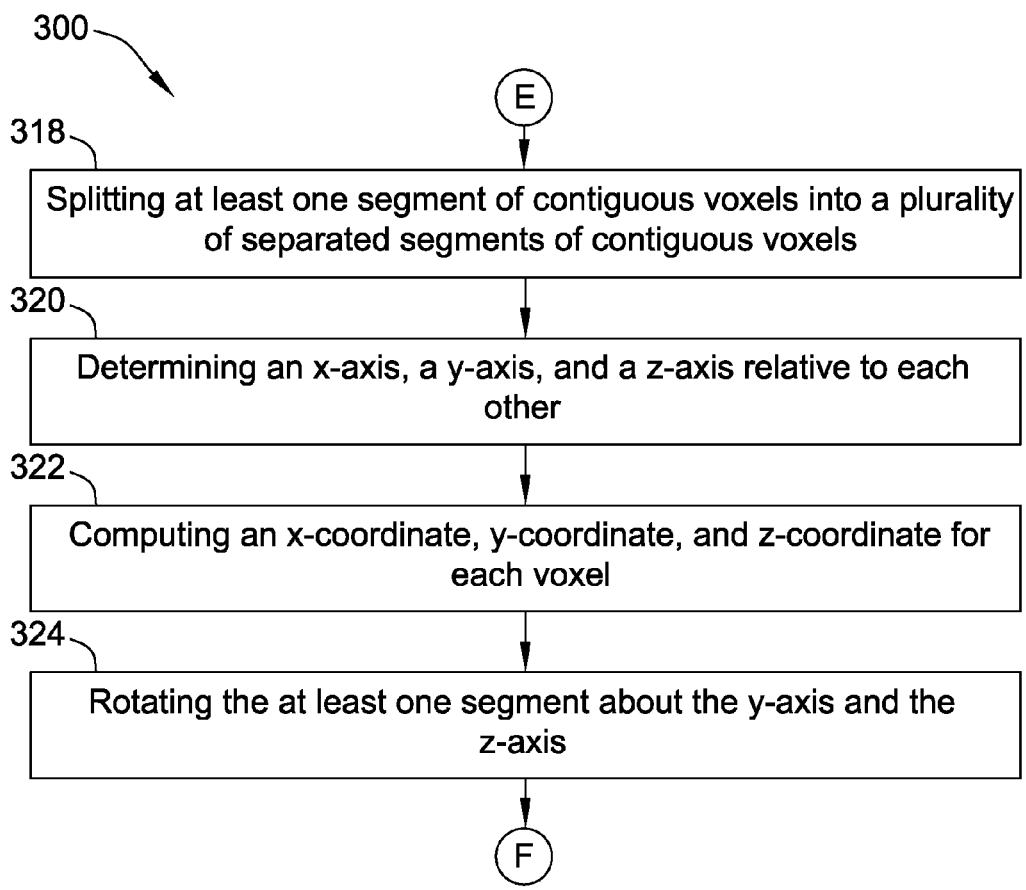
Figure 14:
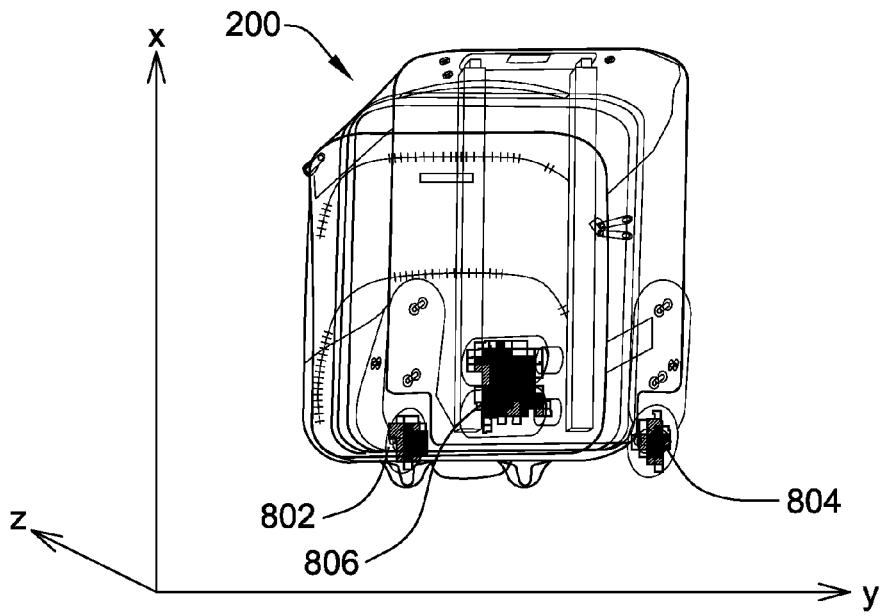

At this point of method 300, it is likely that at least some of the objects that are in close proximity have been joined together in the resulting image. Since method 300 and XDI system 100 ultimately identify materials in the objects based on the measured spectrum, further steps are taken to separate the objects. As such, the subsequent steps facilitate evaluating each segmented object to determine if it can be split into two or more smaller objects. More specifically, the subsequent steps facilitate splitting the pre-existing objects into smaller part based on detected disjointment, i.e., detecting that the object is composed of two or more separate objects, possibly of different material types. The subsequent steps overcome noise FIG. 13 is a continuation of method 300 from FIG. 11. Method 300 also includes splitting 318 at least one segment 806 of contiguous voxels of the plurality of segments of contiguous voxels 802, 804, and 806 (all shown in FIG. 12) into a plurality of separated segments (not shown in FIG. 13) of contiguous voxels, such that each separated segment of contiguous voxels maps onto an associated object 202 and 206. For the remainder of the discussion, segment 806 will be discussed. FIG. 14 is a schematic view of the image shown in FIG. 12 with orthogonal x-, y-, and z-axes. Referring to FIGS. 13 and 14, method 300 includes determining 320 an x-axis, a y-axis, and a z-axis that together span the 3-D space. In the exemplary embodiment, the x-axis, the y-axis, and the z-axis are orthogonal to each other. Alternatively, the x-axis, the y-axis, and the z-axis have any orientation and relationship to each other that enables operation of method 300 and XDI system 100 as described herein. Method 300 further includes computing 322 an x-coordinate, a y-coordinate, and a z-coordinate for each voxel of segment 806. Method 300 also includes rotating 324 segment 806 about the y-axis and the z-axis. For example, in some embodiments, a 3-D position for a center of each voxel is determined for segment 806 and all the points are rotated through a range of angles along the y-axis and the z-axis. Alternatively, any method of voxel rotation is used that enables operation of method 300 and XDI system 100 as described herein.

Although in some embodiments, the images may be very noisy, object separation can be more visible when viewed from specific angles in a volume rendering image display. Due to the bulkiness of the objects, there will be certain view angles that enhances contrast because the path length through the objects in the associated directions maximize the difference between objects and object boundaries. The splitting algorithm takes advantage of this phenomenon observed in volume rendering displays, and takes it one step further by reducing the dimensionality of the data further from two dimensions (in the volume rendering display) to one dimension by looking at different angles of intersection within the volume rendering image.

FIG. 15 is a continuation of method 300 from FIG. 13. FIG. 16 is a graphical representation, i.e., graph 900 of projected sums of intensities of contiguous voxels of segment 806 projected on an x-axis through rotation of segment 806 about the y-axis and the z-axis (all shown in FIG. 14) per method step 324 (shown in FIG. 13). Graph 900 includes a y-axis 902 representative of the projected sums of intensities of segment 806. Y-axis 902 is unitless and includes arbitrary increments. Graph 900 also includes an x-axis 904 representative of position along the x-axis (shown in FIG. 14) onto which the projected sums of intensities is projected. X-axis 904 is divided into a plurality of bins and, in the exemplary embodiment, is unitless and includes arbitrary increments. Graph 900 further includes a curve, i.e., profile 906 representative of the projected sums of intensities of segment 806 as projected onto x-axis 904. Profile 906 defines a minima 908.

Referring to FIGS. 15 and 16, method 300 includes determining 326 projected sums of intensities, on x-axis 904, of segment 806 through rotation of segment 806 about the y-axis and the z-axis (both shown in FIG. 14). In the exemplary embodiment, each predetermined bin on x-axis 904 receives a sum of all of the image values of the voxels whose rotated x-axis value falls within the predetermined range. This creates profile 906. In some embodiments, an anti-aliasing algorithm is used to spread out the contribution from one voxel over x-axis 904 in profile 906 that reduces a potential of aliasing, i.e., introducing artifacts at specific rotation angles.

Method 300 also includes determining 328 at least one minima, e.g., minima 908 on profile 906 of the projected sums of intensities on y-axis 902 that is indicative of object boundaries. The strength of each such minima is quantified and stored for each rotation of segment 806. Over all the rotation angles, the strongest minima are selected.

FIG. 17 is a schematic view of segment 806 of contiguous voxels with a split plane 910 extending therethrough. Split plane 910 is positioned as determined by minima 908 (shown in FIG. 16). Referring to FIGS. 15 and 17, method 300 further includes determining 330 at least one split plane 910 for minima 908. Minima 908 correspond to a plane in 3-D space that defines the optimum cut between two objects for a given rotation of segment 806, i.e., split plane 910. A minimum strength value of minima 908 is required in order to execute the cut. Method 300 also includes splitting 332 segment 806 into a plurality, i.e., two separated segments 912 and 914. In some embodiments, at least partially depending on the number of, the configuration of, and the orientation of the objects under consideration, any number of minima and split planes may be determined.

Figure 18:
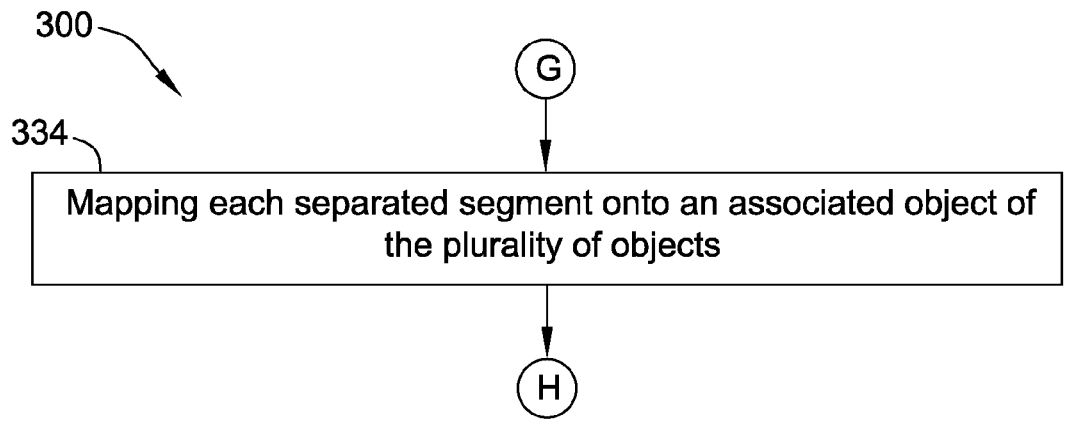
Figure 19:
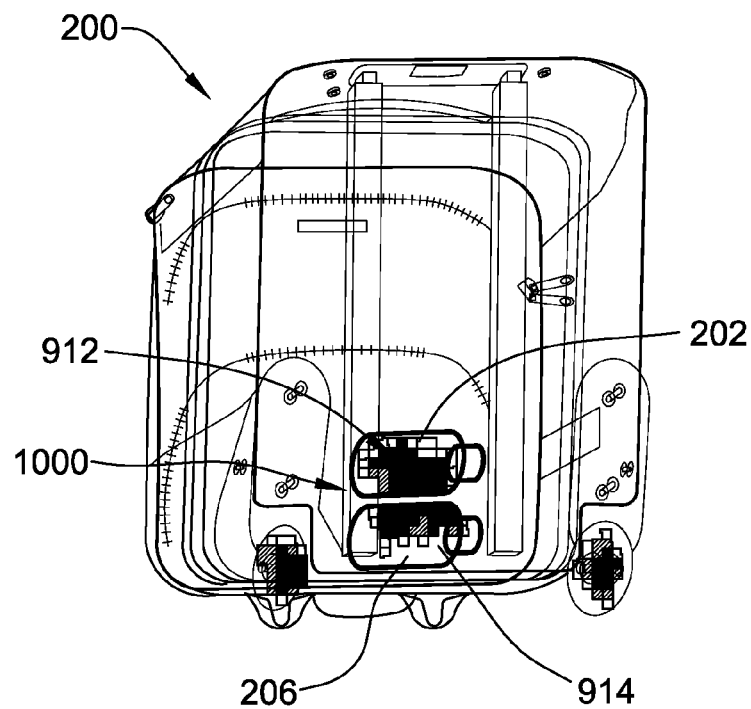

FIG. 18 is a continuation of method 300 from FIG. 15. FIG. 19 is a schematic representation of an exemplary image 1000 of container 200 with separated segments 912 and 914 of contiguous voxels. Referring to FIGS. 18 and 19, method 300 includes mapping 334 each separated segment 912 and 914 of contiguous voxels onto associated objects 202 and 206, respectively.

Figure 20:
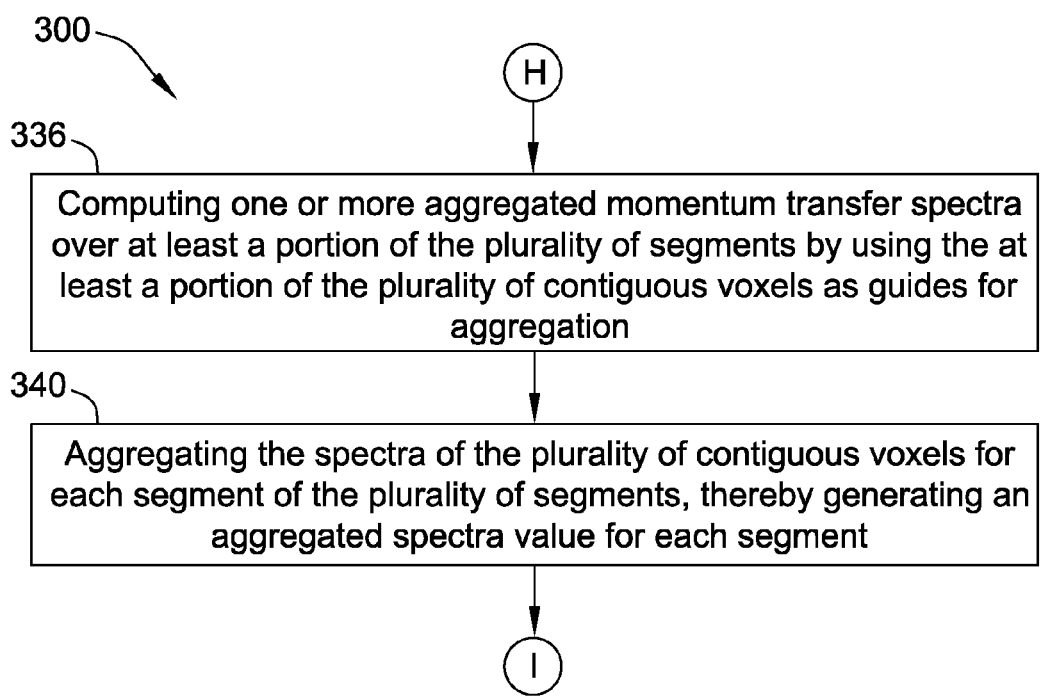

FIG. 20 is a continuation of method 300 from FIG. 18 for some embodiments. Method 300 also includes computing 336 one or more aggregated momentum transfer spectra over at least a portion of the plurality of segments 802, 804, and 806 (shown in FIG. 12) by using at least a portion of the plurality of contiguous voxels 702, 704, and 706 (shown in FIG. 10) as guides for aggregation. Method 300 further includes aggregating 340 the spectra of plurality of contiguous voxels 702, 704, and 706 for each segment of the plurality of segments 802, 804, and 806, thereby generating an aggregated spectra value for each segment.

Figure 21:
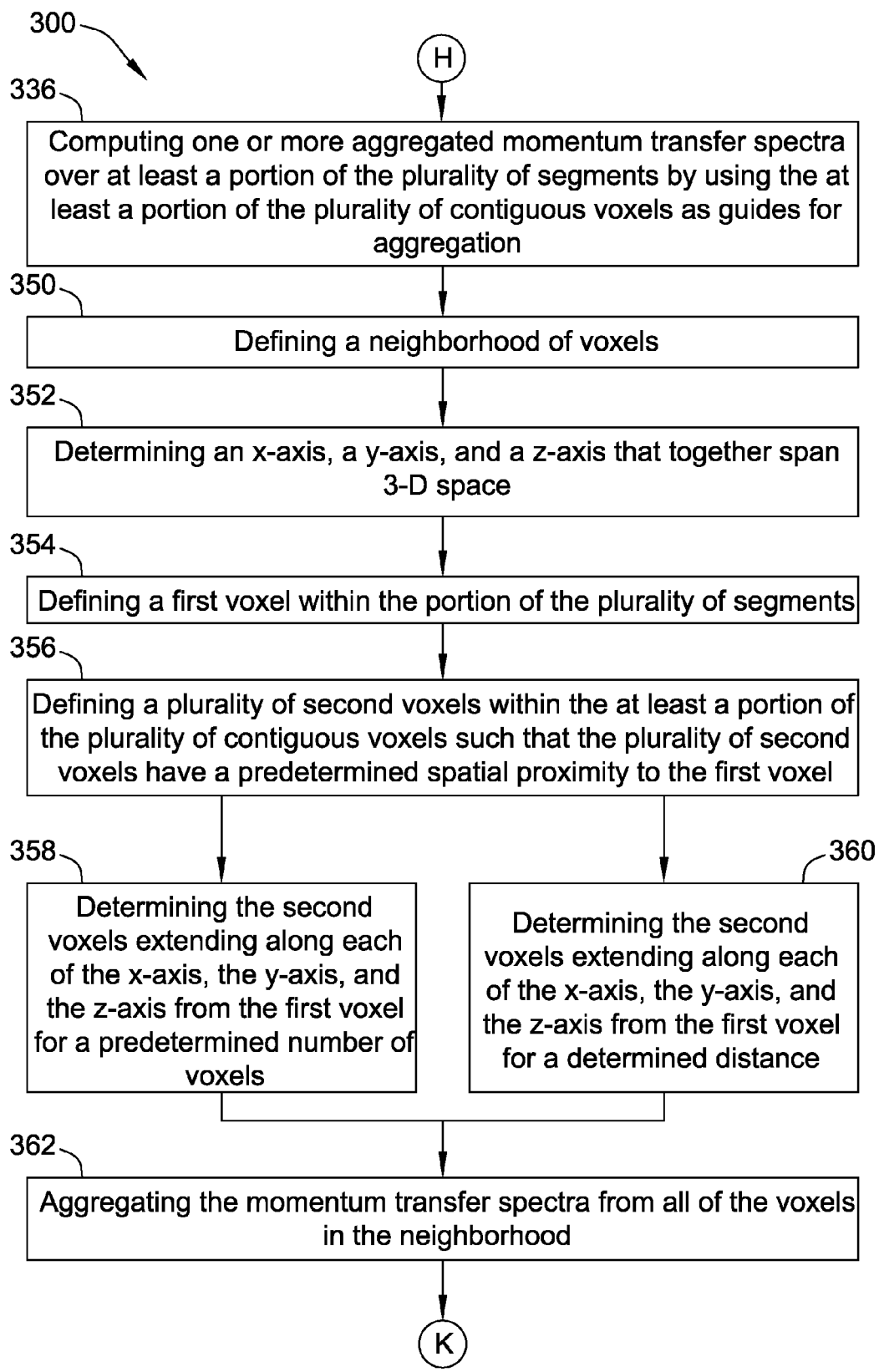

FIG. 21 is a continuation of method 300 from FIG. 18 for yet some further embodiments. Specifically, FIG. 21 describes defining a supervoxel that includes voxels within the object exclusively and including voxels in a neighborhood regardless of association with an object. As such, method 300 also computing 336 one or more aggregated momentum transfer spectra over at least a portion of the plurality of segments 802, 804, and 806 (shown in FIG. 12) by using at least a portion of the plurality of contiguous voxels 702, 704, and 706 (shown in FIG. 10) as guides for aggregation. Method 300 further includes defining 350 a neighborhood (not shown) of voxels that includes determining 352 an x-axis, a y-axis, and a z-axis that together span 3-D space such that an origin is defined at x=0, y=0, and z=0. In the exemplary embodiment, the x-axis, the y-axis, and the z-axis are orthogonal to each other. Alternatively, the x-axis, the y-axis, and the z-axis have any orientation and relationship to each other that enables operation of method 300 and XDI system 100 as described herein.

Defining 350 a neighborhood of voxels also includes defining 352 a central voxel (not shown) within the at least one segment 806 of contiguous voxels. In some embodiments, the central voxel is positioned at the origin. Defining 350 a neighborhood of voxels further includes defining 356 a plurality of second voxels within the at least a portion of the plurality of contiguous voxels 702, 704, and 706 such that the plurality of second voxels have a determined spatial proximity to the first voxel. Defining 350 a neighborhood of voxels also includes at least one of the two following method steps. The first of the two possible method steps includes determining 358 the second voxels extending along each of the x-axis, the y-axis, and the z-axis from the first voxel for a predetermined number of voxels. The second of the possible methods steps includes determining 360 the second voxels extending along each of the x-axis, the y-axis, and the z-axis from the first voxel for a predetermined distance. Method 300 also includes aggregating 362 the momentum transfer spectra from all of the voxels in the neighborhood.

Figure 22:
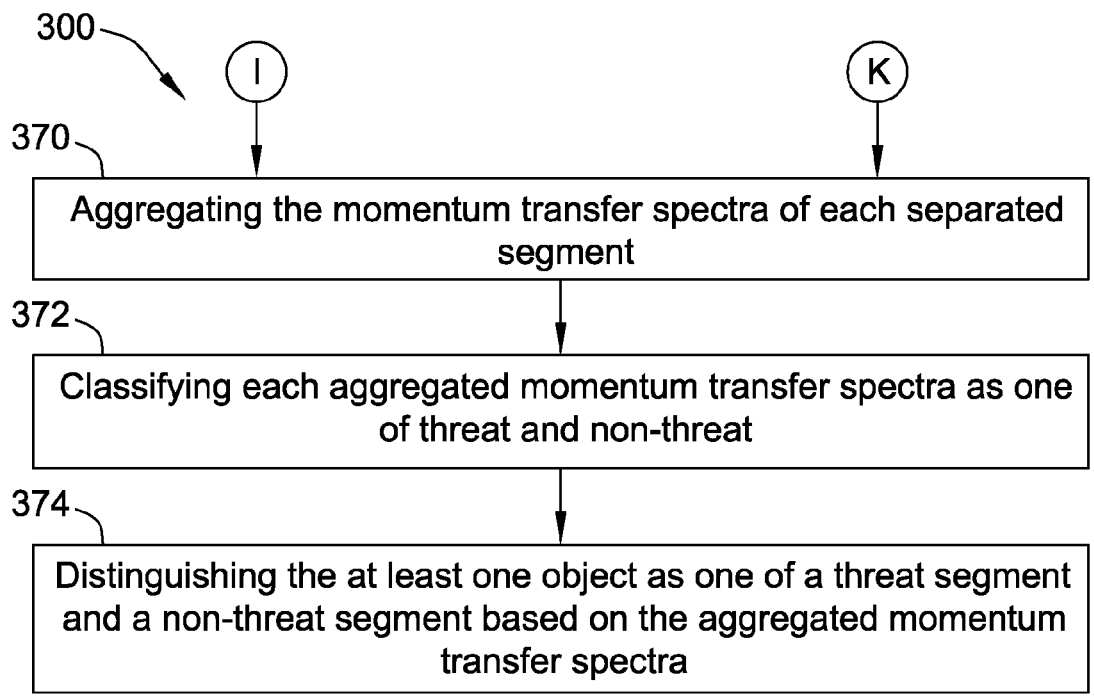
Figure 23:
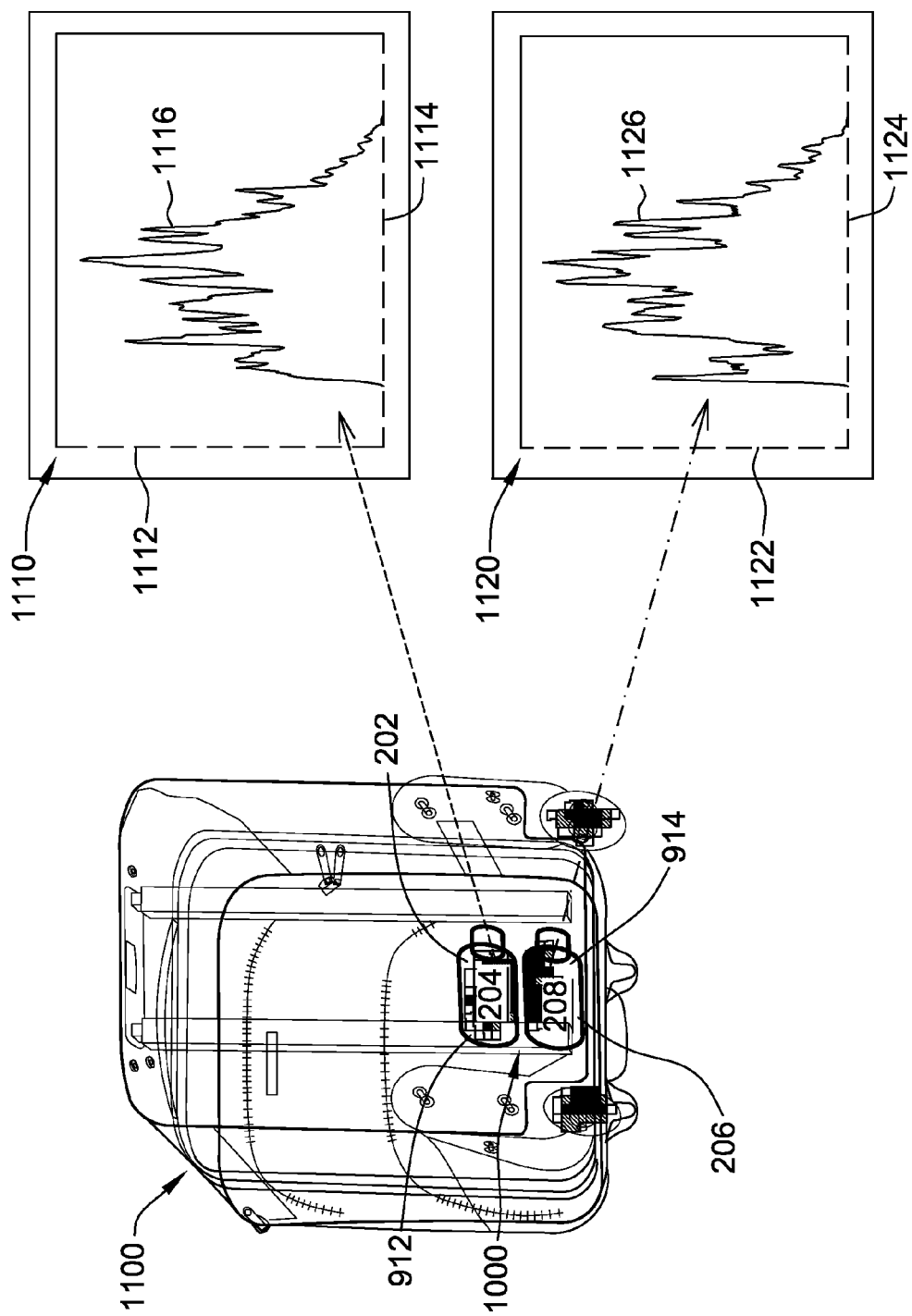

FIG. 22 is a continuation of method 300 from FIGS. 20 and 21. FIG. 23 is a schematic and graphical view of an exemplary image 1100 using XDI system 100 (shown in FIG. 1). Image 1100 includes separated segments 912 and 914 of contiguous voxels mapped onto associated objects 202 and 206, respectively. FIG. 23 includes a first substance identification graph 1110. Graph 1110 includes a y-axis 1112 representative of a relative frequency of entering a value into a momentum transfer bin. Y-axis 1112 is unitless and includes arbitrary increments. Graph 1110 also includes an x-axis 1114 representative of a plurality of momentum transfer bins and, in the exemplary embodiment, is unitless and includes arbitrary increments. Graph 1110 further includes a substance profile curve, i.e., profile 1116 representative of a signature profile of either a threat substance or a non-threat substance. Similarly, FIG. 23 includes a second substance identification graph 1120. Graph 1120 includes a y-axis 1122 representative of a relative frequency of entering a value into a momentum transfer bin. Y-axis 1122 is unitless and includes arbitrary increments. Graph 1120 also includes an x-axis 1124 representative of a plurality of momentum transfer bins and, in the exemplary embodiment, is unitless and includes arbitrary increments. Graph 1120 further includes a substance profile curve, i.e., profile 1126 representative of a signature profile of either a threat substance or a non-threat substance. As used herein, the term "relative frequency" relates to a ration of the number of momentum transfer values in a bin to a total number of momentum transfer values in all of the bins.

Referring to FIGS. 22 and 23, method 300 includes aggregating 370 the momentum transfer spectrum of each separated segment 912 and 914 by aggregating the spectra for all the voxels in objects 202 and 206, respectively. This can be done by a simple averaging or by more sophisticated methods that take into the account the Poisson nature of the data. This step can also be performed on a limited set of the voxels, e.g., without exception, only interior voxels. Method 300 also includes classifying 372 each aggregated momentum transfer spectra as one of threat and non-threat through comparison of substance profile curves 1116 and 1118 with known profiles stored in memory device 186 (shown in FIG. 1). Method 300 further includes distinguishing 374 each of objects 202 and 206 and the associated substances 204 and 208, respectively, as one of a threat segment and a non-threat segment based on the aggregated momentum transfer spectra.

Figure 24:
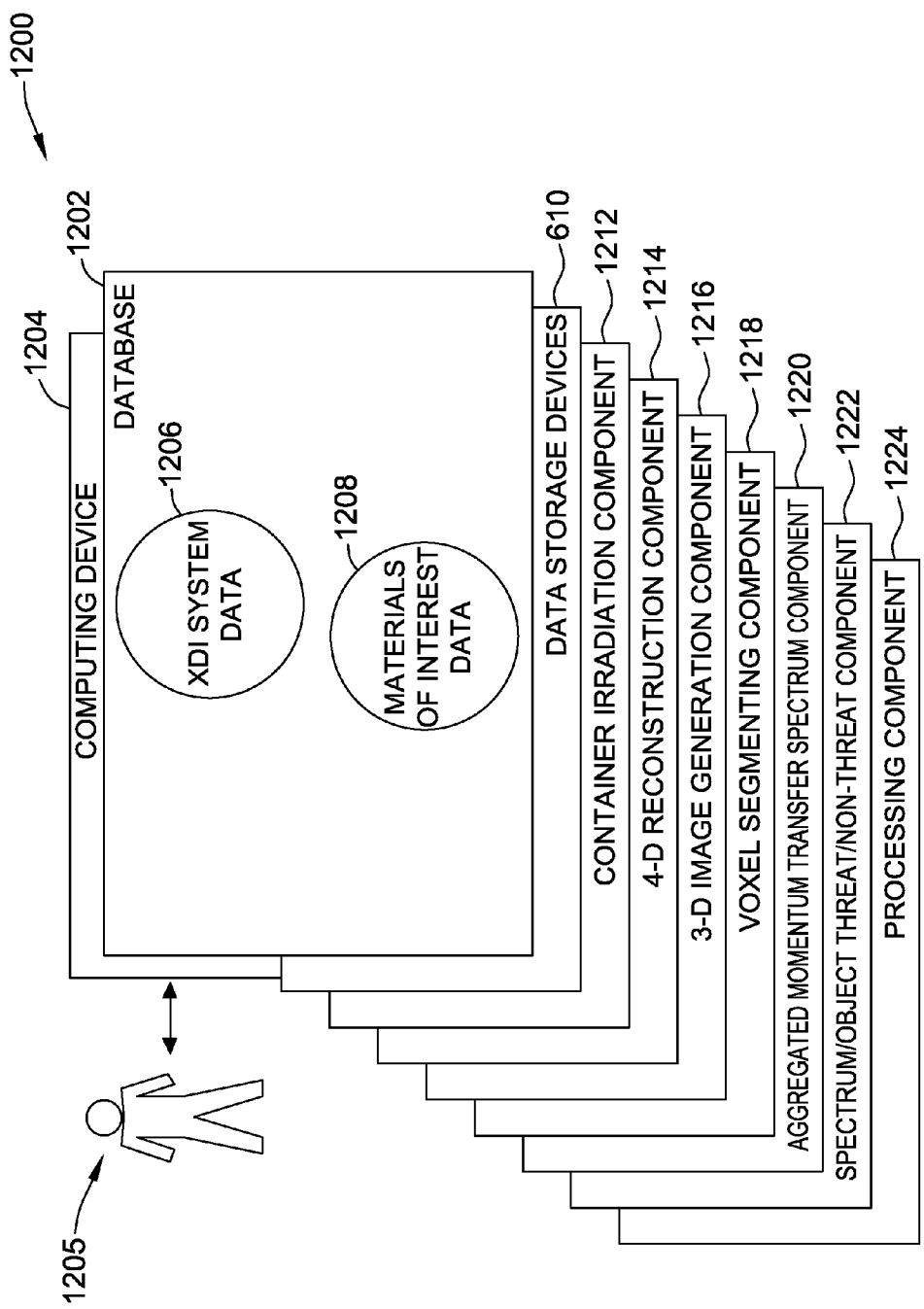

FIG. 24 is an exemplary configuration 1200 of a database 1202 within a computing device 1204, along with other related computing components, that may be used during performing a security inspection of containers as described herein. Database 1202 is coupled to several separate components within computing device 1204, which perform specific tasks. In the exemplary embodiment, computing device 1204 may be computing device 182 (shown in FIG. 1). Computing device 1204 is configured to interface with a human system operator 1205.

In the exemplary embodiment, database 1202 includes XDI system data 1206 and materials of interest data 1208. XDI system data 1206 includes information such as topology configuration information, x-ray power settings, and scatter detector information. Materials of interest data 1208 includes information associated with threat and non-threat materials and substances that are determined during practice of method 300 as described herein.

Computing device 1204 includes database 1202, as well as data storage devices 1210. Computing device 1204 also includes a container irradiation component 1212 for executing method step 302 (shown in FIG. 3), including receiving XDI system data 1206. Computing device 1204 also includes a 4-D reconstruction component 1214 for executing method step 304 (shown in FIG. 3). Computing device 1204 further includes a 3-D image generation component 1216 for executing method steps 306 through 316 (shown in FIGS. 5, 7, 9, and 11). Computing device 1204 also includes a voxel segmenting component 1218 for executing method steps 318 through 334 (shown in FIGS. 13, 15, and 18). Computing device 1204 further includes an aggregated momentum transfer spectrum component 1220 for executing method steps 336 through 370 (shown in FIGS. 20, 21, and 22). Computing device 1204 also includes a spectrum/object threat/non-threat component 1222 for executing method steps 372 and 374 (both shown in FIG. 22). A processing component 1224 assists with execution of computer-executable instructions associated with XDI system 100 and method 300 as described herein.

The above described x-ray diffraction imaging (XDI) systems facilitate cost-effective enhanced identification of materials of interest with a suitably high probability of detection ($P_D$) and low probability of false alarm, i.e., false positive ($P_{FA}$). Specifically, in contrast to many known security scanning systems, the XDI security screening systems as described herein facilitate segmentation of multiple contiguous voxels into segments that may include materials of interest. The initial steps prior to segmentation include generating a scatter strength value for each voxel and filtering the signals for each voxel, thereby decreasing the noise level and improving the homogeneity of those voxels including a single material. The segmentation process includes filtering out voxels with scatter strengths less than a predetermined threshold value that is based on the materials of interest, thereby leaving contiguous voxels with missing voxels in between. The segmentation process also includes a labeling step, where some voxels are retained and some voxels are disregarded, i.e., excluded. The retained voxels are connected and the connected voxels form "islands", i.e., segments of contiguous voxels between the excluded voxels. The segmentation process further includes splitting the segmented segments of contiguous voxels into smaller, individual objects. Moreover, the segmentation process includes computing the spectra for each object through aggregating the spectra of the voxels therein.

As such, the XDI security screening systems as described herein facilitate resolution of individual objects and classification into threat/no threat substances through advanced visual segmentation as a function of aggregating the spectra of contiguous voxels. Specifically, the XDI security screening systems described herein facilitate improved resolution of objects/substances of interest positioned proximate and/or adjacent to each other through joining voxels with predetermined associating characteristics, disregarding voxels without such characteristics, and separating the joined voxels. More specifically, the systems described herein facilitate improved determinations of which voxels to join. Therefore, efficient and effective detection of substances, such as the classes of liquid substances of interest, in cabin baggage screening (CBS) and hold baggage screening (HBS) systems is enhanced A technical effect of the systems and methods described herein includes at least one of: (a) determining voxels associated with objects and/or substances of interest and forming segmented voxel aggregations that facilitate enhanced object resolution and identification of substances of interest; (b) enhancing visual resolution of objects positioned proximate and/or adjacent to each other within checked-in and carry-on luggage and packages and enhancing threat/no threat determinations of such objects and their contents; and (c) determining which voxels of an XDI image construct to keep, disregard, join, and separate.

Exemplary embodiments of x-ray diffraction imaging (XDI) systems are described above in detail. The methods and systems are not limited to the specific embodiments described herein, but rather, components of systems and/or steps of the methods may be utilized independently and separately from other components and/or steps described herein. For example, the methods may also be used in combination with other detection systems and methods, and are not limited to practice with only the detection systems and methods as described herein. Rather, the exemplary embodiment may be implemented and utilized in connection with many other x-ray-based security screening system applications.

Although specific features of various embodiments of the invention may be shown in some drawings and not in others, this is for convenience only. In accordance with the principles of the invention, any feature of a drawing may be referenced and/or claimed in combination with any feature of any other drawing.

Some embodiments involve the use of one or more electronic or computing devices. Such devices typically include a processor or controller, such as a general purpose central processing unit (CPU), a graphics processing unit (GPU), a microcontroller, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method of performing a security inspection of a container including a plurality of objects therein using a computing device including at least one processor coupled to a memory device, said method comprising:
   irradiating the container with polychromatic x-rays;
   reconstructing, using the computing device, a four-dimensional (4-D) voxelized representation of a plurality of scatter cross-sections within the container, wherein the 4-D voxelized representation includes a plurality of voxels, a first three dimensions represent a spatial location of each voxel of the plurality of voxels, and a fourth dimension represents a plurality of momentum transfer values defining a momentum transfer spectrum of the container;
   generating at least one three-dimensional (3-D) image by determining a single value at each voxel of the plurality of voxels as a function of the momentum transfer spectrum;
   segmenting the plurality of voxels into a plurality of segments of contiguous voxels, wherein each segment of the plurality of segments includes a plurality of contiguous voxels, wherein at least a portion of the plurality of segments at least partially maps onto at least one object of the plurality of objects;
   computing one or more aggregated momentum transfer spectra over the at least a portion of the plurality of segments by using at least a portion of the plurality of contiguous voxels as guides for aggregation;
   classifying the one or more aggregated momentum transfer spectra as one of threat and non-threat; and
   distinguishing the at least one object as one of a threat segment and a non-threat segment based on the one or more aggregated momentum transfer spectra.

2. The method in accordance with claim 1, wherein generating at least one 3-D image comprises summing the plurality of scatter cross-sections over substantially all of the plurality of momentum transfer values within the momentum transfer spectrum.

3. The method in accordance with claim 1 further comprising de-noising the plurality of voxels, thereby facilitating a smoothing of the 3-D image.

4. The method in accordance with claim 1, wherein segmenting the plurality of voxels into a plurality of segments of contiguous voxels comprises at least one of:

thresholding each voxel of the plurality of voxels comprising comparing the single value of each voxel of the plurality of voxels to a predetermined threshold value; and performing connected component labeling of each voxel of the plurality of voxels.

5. The method in accordance with claim 4, wherein segmenting the plurality of voxels into a plurality of segments of contiguous voxels further comprises performing image erosion after thresholding each voxel of the plurality of voxels.

6. The method in accordance with claim 1, wherein segmenting the plurality of voxels into a plurality of segments of contiguous voxels further comprises splitting at least one segment of the at least a portion of the plurality of segments into a plurality of separated segments of contiguous voxels.

7. The method in accordance with claim 6, wherein splitting at least one segment of contiguous voxels of the at least a portion of the plurality of segments into a plurality of separated segments of contiguous voxels comprises:
determining an x-axis, a y-axis, and a z-axis that together span 3-D space;
computing an x-coordinate, a y-coordinate, and a z-coordinate for each voxel of the at least one segment;
rotating the at least one segment about the y-axis and the z-axis;
determining a projected sum of intensities, on the x-axis, of the at least one segment through rotation about the y-axis and the z-axis;
determining at least one minima of the projected sum of intensities; and
determining at least one split plane for the at least one minima.

8. The method in accordance with claim 1, wherein computing one or more aggregated momentum transfer spectra over at least a portion of the plurality of segments comprises aggregating the spectra of the plurality of contiguous voxels for each segment of the plurality of segments, thereby generating an aggregated spectra value for each segment.

9. The method in accordance with claim 1, wherein computing one or more aggregated momentum transfer spectra over the at least a portion of the plurality of segments by using at least a portion of the plurality of contiguous voxels as guides for aggregation comprises:
defining a neighborhood of voxels comprising:
defining a first voxel within the at least a portion of the plurality of contiguous voxels; and
defining a plurality of second voxels within the at least a portion of the plurality of contiguous voxels, wherein the plurality of second voxels have a determined spatial proximity to the first voxel; and
aggregating momentum transfer spectra from all of the voxels in the neighborhood.

10. The method in accordance with claim 9, wherein defining a neighborhood of voxels comprises:
determining an x-axis, a y-axis, and a z-axis that together span 3-D space; and
at least one of:
determining the second voxels extending along each of the x-axis, the y-axis, and the z-axis from the first voxel for a predetermined number of voxels; and
determining the second voxels extending along each of the x-axis, the y-axis, and the z-axis from the first voxel for a predetermined distance.

11. An x-ray diffraction imaging (XDI) system comprising:

at least one x-ray source configured to irradiate a container including a plurality of objects therein with polychromatic x-rays;
at least one detector configured to detect scattered x-rays after the polychromatic x-rays have passed through the container; and
a computing device coupled to said at least one detector, said computing device comprising at least one processor and a memory device coupled to said at least one processor, said at least one processor configured to:
reconstruct a four-dimensional (4-D) voxelized representation of a plurality of scatter cross-sections within the container, wherein the 4-D voxelized representation includes a plurality of voxels, a first three dimensions represent a spatial location of each voxel of the plurality of voxels, and a fourth dimension represents a plurality of momentum transfer values defining a momentum transfer spectrum of the container;
generate at least one three-dimensional (3-D) image by determining a single value at each voxel of the plurality of voxels as a function of the momentum transfer spectrum;
segment the plurality of voxels into a plurality of segments of contiguous voxels, wherein each segment of the plurality of segments includes a plurality of contiguous voxels, wherein at least a portion of the plurality of segments at least partially maps onto at least one object of the plurality of objects;
compute one or more aggregated momentum transfer spectra over the at least a portion of the plurality of segments by using the at least a portion of the plurality of contiguous voxels as guides for aggregation;
classify the one or more aggregated momentum transfer spectra as one of threat and non-threat; and
distinguish the at least one object as one of a threat segment and a non-threat segment based on the one or more aggregated momentum transfer spectra.

12. The XDI system in accordance with claim 11, wherein said at least one processor is further configured to generate at least one 3-D image through summing the plurality of scatter cross-sections over substantially all of the plurality of momentum transfer values within the momentum transfer spectrum.

13. The XDI system in accordance with claim 11, wherein said at least one processor is further configured to de-noise the plurality of voxels, thereby facilitating a smoothing of the 3-D image.

14. The XDI system in accordance with claim 11, wherein said at least one processor is further configured to:
threshold each voxel of the plurality of voxels through comparing the single value of each voxel of the plurality of voxels to a predetermined threshold value; and
perform connected component labeling of each voxel of the plurality of voxels.

15. The XDI system in accordance with claim 14, wherein said at least one processor is further configured to perform image erosion after thresholding each voxel of the plurality of voxels.

16. The XDI system in accordance with claim 11, wherein said at least one processor is further configured to split at least one segment of the at least a portion of the plurality of segments into a plurality of separated segments of contiguous voxels.

17. The XDI system in accordance with claim 16, wherein said at least one processor is further configured to:
determine an x-axis, a y-axis, and a z-axis that together span 3-D;

compute an x-coordinate, a y-coordinate, and a z-coordinate for each voxel of the at least one segment;
rotate the at least one segment about the y-axis and the z-axis;
determine a projected sum of intensities, on the x-axis, of the at least one segment through rotation about the y-axis and the z-axis;
determine at least one minima of the projected sum of intensities; and
determine at least one split plane for the at least one minima.

18. The XDI system in accordance with claim 17, wherein said at least one processor is further configured to aggregate the spectra of the plurality of contiguous voxels for each segment of the plurality of segments, thereby generating an aggregated spectra value for each segment.

19. The XDI system in accordance with claim 11, wherein said at least one processor is further configured to:
define a neighborhood of voxels comprising:
defining a first voxel within the at least a portion of the plurality of contiguous voxels; and
defining a plurality of second voxels within the at least a portion of the plurality of contiguous voxels, wherein the plurality of second voxels have a determined spatial proximity to the first voxel; and
aggregating momentum transfer spectra from all of the voxels in the neighborhood.

20. The XDI system in accordance with claim 19, wherein said at least one processor is further configured to:
determine an x-axis, a y-axis, and a z-axis that together span 3-D space; and
at least one of:
determine the second voxels extending along each of the x-axis, the y-axis, and the z-axis from the first voxel for a predetermined number of voxels; and
determine the second voxels extending along each of the x-axis, the y-axis, and the z-axis from the first voxel for a predetermined distance.

21. The XDI system in accordance with claim 11, wherein said XDI system is a multiple inverse fan beam (MIFB) XDI system.

22. One or more non-transitory computer-readable storage media having computer-executable instructions embodied thereon, wherein when executed by at least one processor, the computer-executable instructions cause the at least one processor to:
reconstruct a four-dimensional (4-D) voxelized representation of a plurality of scatter cross-sections within a container, wherein the 4-D voxelized representation includes a plurality of voxels, a first three dimensions represent a spatial location of each voxel of the plurality of voxels, and a fourth dimension represents a plurality of momentum transfer values defining a momentum transfer spectrum of the container;
generate at least one three-dimensional (3-D) image by determining a single value at each voxel of the plurality of voxels as a function of the momentum transfer spectrum;
segment the plurality of voxels into a plurality of segments of contiguous voxels, wherein each segment of the plurality of segments includes a plurality of contiguous voxels, wherein at least a portion of the plurality of segments at least partially maps onto at least one object of the plurality of objects;
compute one or more aggregated momentum transfer spectra over the at least a portion of the plurality of segments by using the at least a portion of the plurality of contiguous voxels as guides for aggregation;
classify the one or more aggregated momentum transfer spectra as one of threat and non-threat; and
distinguish the at least one object as one of a threat segment and a non-threat segment based on the one or more aggregated momentum transfer spectra.

* * * * *